(12) United States Patent
Starksen et al.

(10) Patent No.: US 8,641,727 B2
(45) Date of Patent: Feb. 4, 2014

(54) DEVICES AND METHODS FOR HEART VALVE REPAIR

(75) Inventors: Niel F. Starksen, Los Altos Hills, CA (US); John To, Newark, CA (US)

(73) Assignee: Guided Delivery Systems, Inc., Santa Clara, CA (US)

(*) Notice: Subject to any disclaimer, the term of this patent is extended or adjusted under 35 U.S.C. 154(b) by 1295 days.

(21) Appl. No.: 12/132,161

(22) Filed: Jun. 3, 2008

(65) Prior Publication Data

US 2008/0234728 A1     Sep. 25, 2008

Related U.S. Application Data

(60) Division of application No. 10/741,130, filed on Dec. 19, 2003, now Pat. No. 8,287,555, which is a continuation-in-part of application No. 10/656,797, filed on Sep. 4, 2003, now Pat. No. 7,753,922, and a continuation-in-part of application No. 10/461,043, filed on Jun. 13, 2003, now Pat. No. 6,986,775.

(60) Provisional application No. 60/388,935, filed on Jun. 13, 2002, provisional application No. 60/429,288, filed on Nov. 25, 2002, provisional application No. 60/445,890, filed on Feb. 6, 2003, provisional application No. 60/462,502, filed on Apr. 10, 2003.

(51) Int. Cl.
*A61B 17/10* (2006.01)
*A61F 2/24* (2006.01)

(52) U.S. Cl.
USPC .................. 606/143; 623/2.36; 623/2.37

(58) Field of Classification Search
USPC .................. 606/139, 143, 142; 623/2.11, 623/2.23–2.37; 227/175.1
See application file for complete search history.

(56) References Cited

U.S. PATENT DOCUMENTS

| 2,108,206 A | 2/1938 | Meeker |
| 3,656,185 A | 4/1972 | Carpentier |

(Continued)

FOREIGN PATENT DOCUMENTS

| EP | 0 363 611 A1 | 4/1990 |
| EP | 0 669 101 A1 | 8/1995 |

(Continued)

OTHER PUBLICATIONS

De Simone, R. et al. (Apr. 15, 1993). "Adjustable Tricuspid Valve Annuloplasty Assisted by Intraoperative Transesophageal Color Doppler Echocardiography," *Am. J. Cardiol.* 71(11):926-931.

(Continued)

*Primary Examiner* — Julian W Woo
(74) *Attorney, Agent, or Firm* — Morrison & Foerster LLP

(57) ABSTRACT

Devices and methods provide enhanced treatment of a cardiac valve annulus. Methods generally involve contacting an anchor delivery device with the valve annulus and releasing a plurality of coupled anchors from the anchor delivery device to secure the anchors to the annulus. Anchors, which in some embodiments are super-elastic or shape memory self-securing anchors, are then drawn together to tighten the annulus. Devices generally include an elongate catheter having a housing at or near the distal end for releasably housing a plurality of coupled anchors. The housing may be flexible, may conform to a valve annulus, and in some embodiments may be coupled with an expandable member to enhance contact of the housing with annular tissue. In one embodiment, self-securing anchors lie approximately flat within the delivery device housing, allowing anchors with relatively large deployed shapes to be housed in and deployed from a relatively narrow delivery device.

54 Claims, 19 Drawing Sheets

(56) References Cited

U.S. PATENT DOCUMENTS

| | | |
|---|---|---|
| 3,727,614 A | 4/1973 | Kniazuk |
| 3,773,034 A | 11/1973 | Burns et al. |
| 3,961,419 A | 6/1976 | Schwartz |
| 3,976,079 A | 8/1976 | Samuels et al. |
| 4,014,492 A | 3/1977 | Rothfuss |
| 4,034,473 A | 7/1977 | May |
| 4,042,979 A | 8/1977 | Angell |
| 4,043,504 A | 8/1977 | Hueil et al. |
| 4,053,979 A | 10/1977 | Tuthill et al. |
| 4,055,861 A | 11/1977 | Carpentier et al. |
| 4,069,825 A | 1/1978 | Akiyama |
| 4,290,151 A | 9/1981 | Massana |
| 4,384,406 A | 5/1983 | Tischlinger |
| 4,445,892 A | 5/1984 | Hussein et al. |
| 4,489,446 A | 12/1984 | Reed |
| 4,494,542 A | 1/1985 | Lee |
| 4,619,247 A | 10/1986 | Inoue et al. |
| 4,700,250 A | 10/1987 | Kuriyama |
| 4,726,371 A | 2/1988 | Gibbens |
| 4,758,221 A | 7/1988 | Jureidini |
| 4,784,133 A | 11/1988 | Mackin |
| 4,798,594 A | 1/1989 | Hillstead |
| 4,845,851 A | 7/1989 | Warthen |
| 4,848,341 A | 7/1989 | Ahmad |
| 4,850,354 A | 7/1989 | McGurk-Burleson et al. |
| 4,961,738 A | 10/1990 | Mackin |
| 4,969,893 A | 11/1990 | Swor |
| 4,976,710 A | 12/1990 | Mackin |
| 5,053,047 A | 10/1991 | Yoon |
| 5,064,431 A | 11/1991 | Gilbertson et al. |
| 5,084,058 A | 1/1992 | Li |
| 5,103,804 A | 4/1992 | Abele et al. |
| 5,108,368 A | 4/1992 | Hammerslag et al. |
| 5,133,723 A | 7/1992 | Li et al. |
| 5,221,255 A | 6/1993 | Mahurkar et al. |
| 5,221,269 A | 6/1993 | Miller et al. |
| 5,242,456 A | 9/1993 | Nash et al. |
| 5,242,457 A | 9/1993 | Akopov et al. |
| 5,257,975 A | 11/1993 | Foshee |
| 5,312,341 A | 5/1994 | Turi |
| 5,324,298 A | 6/1994 | Phillips et al. |
| 5,346,500 A | 9/1994 | Suchart |
| 5,358,479 A | 10/1994 | Wilson |
| 5,358,514 A | 10/1994 | Schulman et al. |
| 5,364,407 A | 11/1994 | Poll |
| 5,366,479 A | 11/1994 | McGarry et al. |
| 5,368,591 A | 11/1994 | Lennox et al. |
| 5,383,905 A | 1/1995 | Golds et al. |
| 5,409,483 A | 4/1995 | Campbell et al. |
| 5,409,499 A | 4/1995 | Yi |
| 5,417,700 A | 5/1995 | Egan |
| 5,423,837 A | 6/1995 | Mericle et al. |
| 5,437,680 A | 8/1995 | Yoon |
| 5,439,470 A | 8/1995 | Li |
| 5,450,860 A | 9/1995 | O'Connor |
| 5,452,513 A | 9/1995 | Zinnbauer et al. |
| 5,474,572 A | 12/1995 | Hayhurst |
| 5,484,451 A * | 1/1996 | Akopov et al. ............ 227/175.1 |
| 5,507,760 A | 4/1996 | Wynne et al. |
| 5,520,702 A | 5/1996 | Sauer et al. |
| 5,522,873 A | 6/1996 | Jackman et al. |
| 5,524,630 A | 6/1996 | Crowley |
| 5,527,323 A | 6/1996 | Jervis et al. |
| 5,531,686 A | 7/1996 | Lundquist et al. |
| 5,545,134 A | 8/1996 | Hilaire et al. |
| 5,545,168 A | 8/1996 | Burke |
| 5,565,122 A | 10/1996 | Zinnbauer et al. |
| 5,571,215 A | 11/1996 | Sterman et al. |
| 5,591,194 A | 1/1997 | Berthiaume |
| 5,626,590 A | 5/1997 | Wilk |
| 5,626,614 A | 5/1997 | Hart |
| 5,630,824 A | 5/1997 | Hart |
| 5,643,289 A | 7/1997 | Sauer et al. |
| 5,669,917 A | 9/1997 | Sauer et al. |
| 5,674,279 A | 10/1997 | Wright et al. |
| 5,690,655 A | 11/1997 | Hart et al. |
| 5,709,695 A | 1/1998 | Northrup, III |
| 5,716,370 A | 2/1998 | Williamson, IV et al. |
| 5,718,725 A | 2/1998 | Sterman et al. |
| 5,725,542 A | 3/1998 | Yoon |
| 5,735,290 A | 4/1998 | Sterman et al. |
| 5,741,260 A | 4/1998 | Songer et al. |
| 5,741,301 A | 4/1998 | Pagedas |
| 5,752,518 A | 5/1998 | McGee et al. |
| 5,752,964 A | 5/1998 | Mericle |
| 5,752,966 A | 5/1998 | Chang |
| 5,755,730 A | 5/1998 | Swain et al. |
| 5,766,240 A | 6/1998 | Johnson |
| 5,769,812 A | 6/1998 | Stevens et al. |
| 5,782,861 A | 7/1998 | Cragg et al. |
| 5,810,848 A | 9/1998 | Hayhurst |
| 5,810,853 A | 9/1998 | Yoon |
| 5,817,107 A | 10/1998 | Schaller |
| 5,827,171 A | 10/1998 | Dobak, III et al. |
| 5,843,169 A | 12/1998 | Taheri |
| 5,848,969 A | 12/1998 | Panescu et al. |
| 5,860,992 A | 1/1999 | Daniel et al. |
| 5,860,993 A | 1/1999 | Thompson et al. |
| 5,868,733 A | 2/1999 | Ockuly et al. |
| 5,879,371 A | 3/1999 | Gardiner et al. |
| 5,885,238 A | 3/1999 | Stevens et al. |
| 5,888,240 A | 3/1999 | Carpentier et al. |
| 5,902,321 A | 5/1999 | Caspari et al. |
| 5,904,651 A | 5/1999 | Swanson et al. |
| 5,919,208 A | 7/1999 | Valenti |
| 5,935,149 A | 8/1999 | Ek |
| 5,947,983 A | 9/1999 | Solar et al. |
| 5,961,440 A | 10/1999 | Schweich, Jr. et al. |
| 5,961,539 A | 10/1999 | Northrup, III et al. |
| 5,972,004 A | 10/1999 | Williamson, IV et al. |
| 5,984,933 A * | 11/1999 | Yoon ............................ 606/148 |
| 5,989,284 A | 11/1999 | Laufer |
| 5,991,650 A | 11/1999 | Swanson et al. |
| 6,010,531 A | 1/2000 | Donlon et al. |
| 6,015,428 A | 1/2000 | Pagedas |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,066,160 A | 5/2000 | Colvin et al. |
| 6,074,401 A | 6/2000 | Gardiner et al. |
| 6,077,214 A | 6/2000 | Mortier et al. |
| 6,077,989 A | 6/2000 | Kandel et al. |
| 6,099,553 A | 8/2000 | Hart et al. |
| 6,102,945 A * | 8/2000 | Campbell ..................... 623/2.37 |
| 6,125,852 A | 10/2000 | Stevens et al. |
| 6,149,658 A | 11/2000 | Gardiner et al. |
| 6,162,168 A | 12/2000 | Schweich, Jr. et al. |
| 6,165,183 A | 12/2000 | Kuehn et al. |
| 6,171,329 B1 | 1/2001 | Shaw et al. |
| 6,197,017 B1 | 3/2001 | Brock et al. |
| 6,221,084 B1 | 4/2001 | Fleenor |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,391,048 B1 | 5/2002 | Ginn et al. |
| 6,406,420 B1 | 6/2002 | McCarthy et al. |
| 6,409,743 B1 | 6/2002 | Fenton, Jr. |
| 6,423,088 B1 | 7/2002 | Fenton, Jr. |
| 6,432,123 B2 | 8/2002 | Schwartz et al. |
| 6,461,327 B1 | 10/2002 | Addis et al. |
| 6,514,265 B2 | 2/2003 | Ho et al. |
| 6,524,338 B1 | 2/2003 | Gundry |
| 6,533,753 B1 | 3/2003 | Haarstad et al. |
| 6,551,332 B1 | 4/2003 | Nguyen et al. |

(56) References Cited

U.S. PATENT DOCUMENTS

| | | | |
|---|---|---|---|
| 6,575,971 B2 | 6/2003 | Hauck et al. | |
| 6,575,987 B2 | 6/2003 | Gellman et al. | |
| 6,589,160 B2 | 7/2003 | Schweich, Jr. et al. | |
| 6,602,288 B1 | 8/2003 | Cosgrove et al. | |
| 6,602,289 B1 | 8/2003 | Colvin et al. | |
| 6,607,541 B1 | 8/2003 | Gardiner et al. | |
| 6,613,059 B2 | 9/2003 | Schaller et al. | |
| 6,619,291 B2 | 9/2003 | Hlavka et al. | |
| 6,626,899 B2 | 9/2003 | Houser et al. | |
| 6,629,534 B1 | 10/2003 | St. Goar et al. | |
| 6,641,593 B1 | 11/2003 | Schaller et al. | |
| 6,648,903 B1 | 11/2003 | Pierson, III | |
| 6,651,671 B1 | 11/2003 | Donlon et al. | |
| 6,655,386 B1 | 12/2003 | Makower et al. | |
| 6,669,687 B1 | 12/2003 | Saadat | |
| 6,676,702 B2 | 1/2004 | Mathis | |
| 6,689,164 B1 | 2/2004 | Seguin | |
| 6,699,263 B2 | 3/2004 | Cope | |
| 6,702,826 B2 | 3/2004 | Liddicoat et al. | |
| 6,716,243 B1 | 4/2004 | Colvin et al. | |
| 6,718,985 B2 | 4/2004 | Hlavka et al. | |
| 6,723,038 B1 | 4/2004 | Schroeder et al. | |
| 6,723,107 B1 | 4/2004 | Skiba et al. | |
| 6,733,509 B2 | 5/2004 | Nobles et al. | |
| 6,746,457 B2 | 6/2004 | Dana et al. | |
| 6,749,622 B2 | 6/2004 | McGuckin et al. | |
| 6,752,813 B2 | 6/2004 | Goldfarb et al. | |
| 6,790,231 B2 * | 9/2004 | Liddicoat et al. | 623/2.37 |
| 6,793,618 B2 | 9/2004 | Schweich, Jr. et al. | |
| 6,875,224 B2 | 4/2005 | Grimes | |
| 6,908,424 B2 | 6/2005 | Mortier et al. | |
| 6,923,818 B2 | 8/2005 | Muramatsu et al. | |
| 6,932,792 B1 | 8/2005 | St. Goar et al. | |
| 6,986,775 B2 | 1/2006 | Morales et al. | |
| 6,991,643 B2 | 1/2006 | Saadat | |
| 6,997,931 B2 | 2/2006 | Sauer et al. | |
| 7,004,958 B2 | 2/2006 | Adams et al. | |
| 7,037,334 B1 | 5/2006 | Hlavka et al. | |
| 7,044,957 B2 | 5/2006 | Foerster et al. | |
| 7,048,754 B2 | 5/2006 | Martin et al. | |
| 7,101,395 B2 | 9/2006 | Tremulis et al. | |
| 7,125,421 B2 | 10/2006 | Tremulis et al. | |
| 7,166,127 B2 | 1/2007 | Spence et al. | |
| 7,186,262 B2 | 3/2007 | Saadat | |
| 7,186,264 B2 * | 3/2007 | Liddicoat et al. | 623/2.37 |
| 7,189,199 B2 | 3/2007 | McCarthy et al. | |
| 7,235,086 B2 | 6/2007 | Sauer et al. | |
| 7,241,310 B2 | 7/2007 | Taylor et al. | |
| 7,344,544 B2 | 3/2008 | Bender et al. | |
| 7,452,325 B2 | 11/2008 | Schaller | |
| 7,618,449 B2 | 11/2009 | Tremulis et al. | |
| 7,655,040 B2 * | 2/2010 | Douk et al. | 623/2.37 |
| 7,666,193 B2 | 2/2010 | Starksen et al. | |
| 7,727,247 B2 | 6/2010 | Kimura et al. | |
| 7,753,922 B2 | 7/2010 | Starksen | |
| 7,758,637 B2 | 7/2010 | Starksen et al. | |
| 7,766,812 B2 | 8/2010 | Schroeder et al. | |
| 7,883,538 B2 | 2/2011 | To et al. | |
| 7,922,762 B2 | 4/2011 | Starksen | |
| 7,993,368 B2 | 8/2011 | Gambale et al. | |
| 8,066,766 B2 | 11/2011 | To et al. | |
| 2001/0005787 A1 | 6/2001 | Oz et al. | |
| 2001/0014800 A1 | 8/2001 | Frazier et al. | |
| 2001/0023332 A1 | 9/2001 | Hahnen | |
| 2001/0031979 A1 | 10/2001 | Ricci | |
| 2002/0013621 A1 | 1/2002 | Stobie et al. | |
| 2002/0026201 A1 | 2/2002 | Foerster et al. | |
| 2002/0029080 A1 | 3/2002 | Mortier et al. | |
| 2002/0035361 A1 | 3/2002 | Houser et al. | |
| 2002/0042621 A1 | 4/2002 | Liddicoat et al. | |
| 2002/0065536 A1 | 5/2002 | Hart et al. | |
| 2002/0072757 A1 | 6/2002 | Ahmed et al. | |
| 2002/0087048 A1 | 7/2002 | Brock et al. | |
| 2002/0087049 A1 | 7/2002 | Brock et al. | |
| 2002/0087148 A1 | 7/2002 | Brock et al. | |
| 2002/0087169 A1 * | 7/2002 | Brock et al. | 606/139 |
| 2002/0095167 A1 | 7/2002 | Liddicoat et al. | |
| 2002/0095175 A1 | 7/2002 | Brock et al. | |
| 2002/0138044 A1 | 9/2002 | Streeter et al. | |
| 2002/0156526 A1 | 10/2002 | Hlavka et al. | |
| 2002/0161378 A1 | 10/2002 | Downing | |
| 2002/0165486 A1 | 11/2002 | Bertolero et al. | |
| 2002/0173841 A1 | 11/2002 | Ortiz et al. | |
| 2002/0193815 A1 | 12/2002 | Foerster et al. | |
| 2003/0009196 A1 | 1/2003 | Peterson | |
| 2003/0018358 A1 | 1/2003 | Saadat | |
| 2003/0032979 A1 | 2/2003 | Mortier et al. | |
| 2003/0033006 A1 | 2/2003 | Phillips et al. | |
| 2003/0060813 A1 | 3/2003 | Loeb et al. | |
| 2003/0069593 A1 | 4/2003 | Tremulis et al. | |
| 2003/0074012 A1 | 4/2003 | Nguyen et al. | |
| 2003/0078465 A1 | 4/2003 | Pai et al. | |
| 2003/0078603 A1 | 4/2003 | Schaller et al. | |
| 2003/0093118 A1 | 5/2003 | Ho et al. | |
| 2003/0105520 A1 | 6/2003 | Alferness et al. | |
| 2003/0125739 A1 | 7/2003 | Bagga et al. | |
| 2003/0125767 A1 | 7/2003 | Collier et al. | |
| 2003/0130731 A1 | 7/2003 | Vidlund et al. | |
| 2003/0144697 A1 | 7/2003 | Mathis et al. | |
| 2003/0158464 A1 | 8/2003 | Bertolero | |
| 2003/0158581 A1 | 8/2003 | Levinson | |
| 2003/0167062 A1 | 9/2003 | Gambale et al. | |
| 2003/0167071 A1 | 9/2003 | Martin et al. | |
| 2003/0199974 A1 | 10/2003 | Lee et al. | |
| 2003/0220685 A1 | 11/2003 | Hlavka et al. | |
| 2003/0225420 A1 | 12/2003 | Wardle | |
| 2003/0233105 A1 | 12/2003 | Gayton | |
| 2003/0233142 A1 | 12/2003 | Morales et al. | |
| 2003/0236535 A1 | 12/2003 | Onuki et al. | |
| 2004/0003819 A1 | 1/2004 | St. Goar et al. | |
| 2004/0019378 A1 | 1/2004 | Hlavka et al. | |
| 2004/0030382 A1 | 2/2004 | St. Goar et al. | |
| 2004/0039442 A1 | 2/2004 | St. Goar et al. | |
| 2004/0092962 A1 | 5/2004 | Thornton et al. | |
| 2004/0093024 A1 | 5/2004 | Lousararian et al. | |
| 2004/0097788 A1 | 5/2004 | Mourlas et al. | |
| 2004/0122450 A1 | 6/2004 | Oren et al. | |
| 2004/0172046 A1 | 9/2004 | Hlavka et al. | |
| 2004/0181238 A1 | 9/2004 | Zarbatany et al. | |
| 2004/0186378 A1 | 9/2004 | Gesswein | |
| 2004/0193191 A1 | 9/2004 | Starksen et al. | |
| 2004/0204724 A1 | 10/2004 | Kissel et al. | |
| 2004/0210238 A1 | 10/2004 | Nobles et al. | |
| 2004/0236372 A1 | 11/2004 | Anspach, III et al. | |
| 2004/0236419 A1 | 11/2004 | Milo | |
| 2004/0243227 A1 | 12/2004 | Starksen et al. | |
| 2005/0021054 A1 | 1/2005 | Ainsworth et al. | |
| 2005/0055052 A1 | 3/2005 | Lombardo et al. | |
| 2005/0055087 A1 | 3/2005 | Starksen | |
| 2005/0065550 A1 | 3/2005 | Starksen et al. | |
| 2005/0075723 A1 | 4/2005 | Schroeder et al. | |
| 2005/0080454 A1 | 4/2005 | Drews et al. | |
| 2005/0107810 A1 | 5/2005 | Morales et al. | |
| 2005/0107811 A1 | 5/2005 | Starksen et al. | |
| 2005/0107812 A1 | 5/2005 | Starksen et al. | |
| 2005/0107871 A1 | 5/2005 | Realyvasquez et al. | |
| 2005/0119523 A1 | 6/2005 | Starksen et al. | |
| 2005/0119673 A1 | 6/2005 | Gordon et al. | |
| 2005/0137689 A1 | 6/2005 | Salahieh et al. | |
| 2005/0184122 A1 | 8/2005 | Hlavka et al. | |
| 2005/0192599 A1 | 9/2005 | Demarais | |
| 2005/0192629 A1 | 9/2005 | Saadat et al. | |
| 2005/0197694 A1 | 9/2005 | Pai et al. | |
| 2005/0209690 A1 | 9/2005 | Mathis et al. | |
| 2005/0216078 A1 | 9/2005 | Starksen et al. | |
| 2005/0228452 A1 | 10/2005 | Mourlas et al. | |
| 2005/0251157 A1 | 11/2005 | Saadat et al. | |
| 2005/0251159 A1 | 11/2005 | Ewers et al. | |
| 2005/0251166 A1 | 11/2005 | Vaughan et al. | |
| 2005/0251177 A1 | 11/2005 | Saadat et al. | |
| 2005/0251205 A1 | 11/2005 | Ewers et al. | |
| 2005/0251207 A1 | 11/2005 | Flores et al. | |
| 2005/0251208 A1 | 11/2005 | Elmer et al. | |
| 2005/0251209 A1 | 11/2005 | Saadat et al. | |

(56) References Cited

U.S. PATENT DOCUMENTS

| | | |
|---|---|---|
| 2005/0251210 A1 | 11/2005 | Westra et al. |
| 2005/0267495 A1 | 12/2005 | Ginn et al. |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0015144 A1 | 1/2006 | Burbank et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0122633 A1 | 6/2006 | To et al. |
| 2006/0129188 A1 | 6/2006 | Starksen et al. |
| 2006/0161040 A1 | 7/2006 | McCarthy et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0241656 A1 | 10/2006 | Starksen et al. |
| 2006/0264975 A1 | 11/2006 | Pipenhagen et al. |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010857 A1 | 1/2007 | Sugimoto et al. |
| 2007/0032820 A1 | 2/2007 | Chin-Chen et al. |
| 2007/0038293 A1 | 2/2007 | St.Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0112422 A1 | 5/2007 | Dehdashtian |
| 2007/0112424 A1 | 5/2007 | Spence et al. |
| 2008/0045977 A1 | 2/2008 | To et al. |
| 2008/0045982 A1 | 2/2008 | To et al. |
| 2008/0045983 A1 | 2/2008 | To et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058868 A1 | 3/2008 | To et al. |
| 2008/0234815 A1 | 9/2008 | Starksen |
| 2008/0294177 A1 | 11/2008 | To et al. |
| 2009/0182417 A1 | 7/2009 | Tremulis et al. |
| 2009/0222083 A1 | 9/2009 | Nguyen et al. |
| 2009/0234318 A1 | 9/2009 | Loulmet et al. |
| 2009/0276038 A1 | 11/2009 | Tremulis et al. |
| 2010/0049213 A1 | 2/2010 | Serina et al. |
| 2010/0076548 A1 | 3/2010 | Konno |
| 2010/0082098 A1 | 4/2010 | Starksen et al. |
| 2010/0094314 A1 | 4/2010 | Hernlund et al. |
| 2010/0121349 A1 | 5/2010 | Meier et al. |
| 2011/0160528 A1 | 6/2011 | Starksen |

FOREIGN PATENT DOCUMENTS

| | | |
|---|---|---|
| JP | 6-510460 A | 11/1994 |
| JP | 11-506628 A | 6/1999 |
| JP | 2004-601 A | 1/2004 |
| JP | 2007-514455 A | 6/2007 |
| WO | WO-93/08740 A1 | 5/1993 |
| WO | WO-94/03227 A1 | 2/1994 |
| WO | WO-95/15715 A1 | 6/1995 |
| WO | WO-96/08208 A1 | 3/1996 |
| WO | WO-96/39081 A1 | 12/1996 |
| WO | WO-96/39942 A1 | 12/1996 |
| WO | WO-97/27799 A1 | 8/1997 |
| WO | WO-97/27807 A1 | 8/1997 |
| WO | WO-98/07375 A1 | 2/1998 |
| WO | WO-00/60995 A2 | 10/2000 |
| WO | WO-00/60995 A3 | 10/2000 |
| WO | WO-00/67640 A2 | 11/2000 |
| WO | WO-00/67640 A3 | 11/2000 |
| WO | WO-01/26586 A1 | 4/2001 |
| WO | WO-01/54618 A1 | 8/2001 |
| WO | WO-02/03892 A1 | 1/2002 |
| WO | WO-02/051329 A1 | 7/2002 |
| WO | WO-02/085251 A1 | 10/2002 |
| WO | WO-02/085252 A1 | 10/2002 |
| WO | WO-03/088875 A1 | 10/2003 |
| WO | WO-03/105667 A2 | 12/2003 |
| WO | WO-03/105667 A3 | 12/2003 |
| WO | WO-03/105670 A2 | 12/2003 |
| WO | WO-03/105670 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2005/025644 A2 | 3/2005 |
| WO | WO-2005/025644 A3 | 3/2005 |
| WO | WO-2005/062931 A2 | 7/2005 |
| WO | WO-2005/062931 A3 | 7/2005 |
| WO | WO-2005/102181 A1 | 11/2005 |
| WO | WO-2006/034243 A2 | 3/2006 |
| WO | WO-2006/034243 A3 | 3/2006 |
| WO | WO-2006/037073 A2 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C2 | 11/2006 |
| WO | WO-2007/005495 A1 | 1/2007 |
| WO | WO-2007/021564 A1 | 2/2007 |
| WO | WO-2007/021834 A1 | 2/2007 |
| WO | WO-2007/035449 A2 | 3/2007 |
| WO | WO-2007/056502 A1 | 5/2007 |
| WO | WO-2007/100409 A2 | 9/2007 |
| WO | WO-2008/028135 A2 | 3/2008 |
| WO | WO-2008/028135 A3 | 3/2008 |

OTHER PUBLICATIONS

De Simone, R. et al. (Apr. 1, 1994). "Adjustable Annuloplasty for Tricuspid Insufficiency with External Control," *Reader's Comments and Reply, Am. J. Cardiol.* 73(9):721-722.

Downing, S.W. et al. (2002). "Feasibility of Off-Pump ASD Closure Using Real-Time 3-D Echocardiography," *The Heart Surgery Forum* 5(2):96-99, Abstract 7025.

Final Office Action mailed on Feb. 6, 2007, for U.S. Appl. No. 10/656,797, filed Sep. 4, 2003, 8 pages.

Final Office Action mailed on Jul. 12, 2007, for U.S. Appl. No. 11/202,474, filed Aug. 11, 2005, 10 pages.

Final Office Action mailed on Jul. 24, 2007, for U.S. Appl. No. 10/741,130, filed Dec. 19, 2003, 10 pages.

Final Office Action mailed on Aug. 6, 2007, for U.S. Appl. No. 10/901,019, filed Jul. 27, 2004, 12 pages.

Final Office Action mailed on Aug. 6, 2007, for U.S. Appl. No. 11/137,833, filed May 24, 2005, 8 pages.

Final Office Action mailed on Aug. 13, 2007, for U.S. Appl. No. 10/900,980, filed Jul. 27, 2004, 9 pages.

Final Office Action mailed on Aug. 14, 2007, for U.S. Appl. No. 11/255,400 filed Oct. 20, 2005, 8 pages.

Final Office Action mailed on Aug. 30, 2007, for U.S. Appl. No. 11/232,190 filed Sep. 20, 2005, 9 pages.

Final Office Action mailed on Oct. 30, 2007, for U.S. Appl. No. 10/656,797, filed Sep. 4, 2003, 6 pages.

Final Office Action mailed on Apr. 2, 2008, for U.S. Appl. No. 10/792,681, filed Mar. 2, 2004, 15 pages.

Final Office Action mailed on Apr. 14, 2008, for U.S. Appl. No. 10/091,019, filed Jul. 27, 2004, 11 pages.

Final Office Action mailed on May 28, 2008, for U.S. Appl. No. 11/270,034, filed Nov. 8, 2005, 10 pages.

Final Office Action mailed on Jun. 4, 2008, for U.S. Appl. No. 11/202,474, filed Aug. 11, 2005, 10 pages.

International Search Report mailed Dec. 19, 2006, for PCT Application No. PCT/US2006/031190, filed Aug. 10, 2006, four pages.

International Search Report mailed on Apr. 2, 2007, for PCT Application No. PCT/US2006/043597, filed Nov. 8, 2006, seven pages.

Nagy, Z.L. et al. (Dec. 2000). "Mitral Annuloplasty with a Suture Technique," *European Journal of Cardio-thoracic Surgery* 18(6):739-740.

(56) References Cited

OTHER PUBLICATIONS

Non-Final Office Action mailed on Aug. 9, 2006, for U.S. Appl. No. 10/900,980, filed Jul. 27, 2004, 17 pages.
Non-Final Office Action mailed on Aug. 22, 2006, for U.S. Appl. No. 10/656,797, filed Sep. 4, 2003, 6 pages.
Non-Final Office Action mailed on Nov. 15, 2006, for U.S. Appl. No. 11/137,833, filed May 24, 2005, 12 pages.
Non-Final Office Action mailed on Nov. 28, 2006, for U.S. Appl. No. 10/901,019, filed Jul. 27, 2004, 20 pages.
Non-Final Office Action mailed on Dec. 27, 2006, for U.S. Appl. No. 10/741,130, filed Dec. 19, 2003, 9 pages.
Non-Final Office Action mailed on Dec. 27, 2006, for U.S. Appl. No. 11/270,034 filed Nov. 8, 2005, 8 pages.
Non-Final Office Action mailed on Jan. 4, 2007, for U.S. Appl. No. 11/255,400 filed Oct. 20, 2005, 7 pages.
Non-Final Office Action mailed on Feb. 27, 2007, for U.S. Appl. No. 11/202,474, filed Aug. 11, 2005, 8 pages.
Non-Final Office Action mailed on Mar. 12, 2007, for U.S. Appl. No. 11/232,190 filed Sep. 20, 2005, 11 pages.
Non-Final Office Action mailed on Jul. 24, 2007, for U.S. Appl. No. 10/656,797, filed Sep. 4, 2003, 6 pages.
Non-Final Office Action mailed on Aug. 1, 2007, for U.S. Appl. No. 10/792,681, filed Mar. 2, 2004, 16 pages.
Non-Final Office Action mailed on Aug. 30, 2007, for U.S. Appl. No. 11/270,034 filed Nov. 8, 2005, 10 pages.
Non-Final Office Action mailed on Oct. 19, 2007, for U.S. Appl. No. 11/202,474, filed Aug. 11, 2005, 7 pages.
Non-Final Office Action mailed on Oct. 29, 2007, for U.S. Appl. No. 10/901,019, filed Jul. 27, 2004, 10 pages.
Non-Final Office Action mailed on Nov. 14, 2007, for U.S. Appl. No. 10/741,130, filed Dec. 19, 2003, 8 pages.
Non-Final Office Action mailed on Nov. 14, 2007, for U.S. Appl. No. 11/137,833, filed May 24, 2005, 8 pages.
Non-Final Office Action mailed Jan. 9, 2008, for U.S. Appl. No. 11/232,190, filed Sep. 20, 2005, 8 pages.
Non-Final Office Action mailed Jan. 31, 2008, for U.S. Appl. No. 11/255,400, filed Oct. 20, 2005, 7 pages.
Non-Final Office Action (Supplementary) mailed on May 9, 2008, for U.S. Appl. No. 11/255,400, filed Oct. 20, 2005, 7 pages.
Non-Final Office Action mailed on Mar. 27, 2008, for U.S. Appl. No. 10/900,980, filed Jul. 27, 2004, 7 pages.
Non-Final Office Action mailed on Jun. 6, 2008, for U.S. Appl. No. 10/656,797, filed Sep. 4, 2003, 5 pages.
Shumway, S.J. et al. (Dec. 1988). "A 'Designer' Annuloplasty Ring for Patients with Massive Mitral Annular Dilatation," *Ann. Thorac. Surg.* 46(6):695-696.
U.S. Appl. No. 11/656,141, filed Jan. 19, 2007, by Straksen et al.
U.S. Appl. No. 11/875,774, filed Oct. 19, 2007, by Serina et al.
U.S. Appl. No. 12/132,375, filed Jun. 3, 2008, by Starksen et al.
Final Office Action mailed on Jan. 22, 2009, for U.S. Appl. No. 11/255,400, filed Oct. 20, 2005, 8 pages.
Final Office Action mailed on Mar. 11, 2009, for U.S. Appl. No. 10/656,797, filed Sep. 4, 2003, 10 pages.
Final Office Action mailed on Apr. 10, 2009, for U.S. Appl. No. 11/414,657, filed Apr. 27, 2006, 8 pages.
Final Office Action mailed on Apr. 10, 2009, for U.S. Appl. No. 11/255,400, filed Oct. 20, 2005, 8 pages.
Final Office Action mailed on Apr. 29, 2009, for U.S. Appl. No. 10/901,019, filed Jul. 27, 2004, 9 pages.
Non-Final Office Action mailed on Jan. 13, 2009, for U.S. Appl. No. 10/901,555, filed Jul. 27, 2004, 11 pages.
Non-Final Office Action mailed on Jan. 23, 2009, for U.S. Appl. No. 11/232,190, filed Sep. 20, 2005, 8 pages.
Non-Final Office Action mailed on Jan. 23, 2009, for U.S. Appl. No. 11/270,034, filed Nov. 8, 2005, 8 pages.
Non-Final Office Action mailed on Jan. 29, 2009, for U.S. Appl. No. 10/900,980, filed Jul. 27, 2004, 6 pages.
Non-Final Office Action mailed on Mar. 5, 2009, for U.S. Appl. No. 11/202,474, filed Aug. 11, 2005, 10 pages.
Non-Final Office Action mailed on Mar. 18, 2009, for U.S. Appl. No. 10/901,554, filed Jul. 27, 2004, 12 pages.
Non-Final Office Action mailed on Mar. 27, 2009, for U.S. Appl. No. 10/741,130, filed Dec. 19, 2003, 9 pages.
Non-Final Office Action mailed on Mar. 31, 2009, for U.S. Appl. No. 10/792,681, filed Mar. 2, 2004, 15 pages.
Final Office Action mailed on Aug. 1, 2008, for U.S. Appl. No. 11/232,190, filed Sep. 20, 2005, 8 pages.
Final Office Action mailed on Sep. 30, 2008, for U.S. Appl. No. 10/900,980, filed Jul. 27, 2004, 7 pages.
Final Office Action mailed on Oct. 14, 2008, for U.S. Appl. No. 10/741,130, filed Dec. 19, 2003, 9 pages.
Non-Final Office Action mailed on Aug. 29, 2008, for U.S. Appl. No. 10/792,681, filed Mar. 2, 2004, 15 pages.
Non-Final Office Action mailed on Sep. 26, 2008, for U.S. Appl. No. 11/414,657, filed Apr. 27, 2006, 11 pages.
Non-Final Office Action mailed on Oct. 24, 2008, for U.S. Appl. No. 10/901,019, filed Jul. 27, 2004, 11 pages.
Supplementary European Search Report mailed on Nov. 10, 2008, for EP Application No. 04 78 2847, filed on Sep. 1, 2004, 2 pages.
U.S. Appl. No. 12/187,331, filed Aug. 6, 2008, by To et al.
European Examination Communication mailed on Dec. 8, 2009, for EP Application No. 06 837 222.6 filed on Nov. 8, 2006, three pages.
Extended European Search Report mailed on Sep. 9, 2011, for EP Patent Application No. 11158896.8, filed on Sep. 1, 2004, 7 pages.
Extended European Search Report mailed on Sep. 16, 2011, for EP Patent Application No. 11158898.4, filed on Sep. 1, 2004, 8 pages.
Final Office Action mailed on Jul. 21, 2009, for U.S. Appl. No. 11/270,034, filed Nov. 8, 2005, 8 pages.
Final Office Action mailed on Sep. 2, 2009, for U.S. Appl. No. 11/232,190, filed Sep. 20, 2005, 8 pages.
Final Office Action mailed on Sep. 28, 2009, for U.S. Appl. No. 11/202,474, filed Aug. 11, 2005, 10 pages.
Final Office Action mailed on Oct. 13, 2009, for U.S. Appl. No. 10/901,554, filed Jul. 27, 2004, 11 pages.
Final Office Action mailed on Nov. 10, 2009, for U.S. Appl. No. 10/741,130, filed Dec. 19, 2003, 9 pages.
Final Office Action mailed on Mar. 3, 2010, for U.S. Appl. No. 11/414,657, filed Apr. 27, 2006, 7 pages.
Final Office Action mailed on Mar. 25, 2010, for U.S. Appl. No. 10/900,980, filed Jul. 27, 2004, 8 pages.
Final Office Action mailed on Jun. 8, 2010, for U.S. Appl. No. 10/792,681, filed Mar. 2, 2004, 17 pages.
Final Office Action mailed on Jul. 26, 2010, for U.S. Appl. No. 11/270,034, filed Nov. 8, 2005, 8 pages.
Final Office Action mailed on Sep. 15, 2010, for U.S. Appl. No. 11/894,401, filed Aug. 20, 2007, 6 pages.
Final Office Action mailed on Oct. 6, 2010, for U.S. Appl. No. 12/132,375, filed Jun. 3, 2008, 9 pages.
Final Office Action mailed on Nov. 26, 2010, for U.S. Appl. No. 11/894,340, filed Aug. 20, 2007, 12 pages.
Final Office Action mailed on Nov. 29, 2010, for U.S. Appl. No. 11/894,463, filed Aug. 20, 2007, 12 pages.
Final Office Action mailed on Feb. 24, 2011, for U.S. Appl. No. 11/894,397, filed Aug. 20, 2007, 12 pages.
Final Office Action mailed on Feb. 24, 2011, for U.S. Appl. No. 11/894,468, filed Aug. 20, 2007, 12 pages.
Final Office Action mailed on Mar. 17, 2011, for U.S. Appl. No. 10/901,554, filed Jul. 27, 2004, 13 pages.
Final Office Action mailed on Mar. 17, 2011, for U.S. Appl. No. 11/202,474, filed Aug. 11, 2005, 9 pages.
Final Office Action mailed on Apr. 20, 2011, for U.S. Appl. No. 11/414,657, filed Apr. 27, 2006, 8 pages.
Final Office Action mailed on Aug. 4, 2011, for U.S. Appl. No. 10/900,980, filed Jul. 27, 2004, 9 pages.
Final Office Action mailed on Nov. 3, 2011, for U.S. Appl. No. 12/581,040, filed Oct. 16, 2009, 5 pages.
Final Office Action mailed on Nov. 10, 2011, for U.S. Appl. No. 10/792,681, filed Mar. 2, 2004, 20 pages.
Final Office Action mailed on Dec. 6, 2011, for U.S. Appl. No. 12/366,553, filed Feb. 5, 2009, 7 pages.
Non-Final Office Action mailed on Aug. 25, 2009, for U.S. Appl. No. 10/900,980, filed Jul. 27, 2004, 7 pages.

(56) References Cited

OTHER PUBLICATIONS

Non-Final Office Action mailed on Aug. 26, 2009, for U.S. Appl. No. 11/414,657, filed Apr. 27, 2006, 6 pages.
Non-Final Office Action mailed on Sep. 17, 2009, for U.S. Appl. No. 10/656,797, filed Sep. 4, 2003, 13 pages.
Non-Final Office Action mailed on Oct. 19, 2009, for U.S. Appl. No. 10/901,019, filed Jul. 27, 2004, 21 pages.
Non-Final Office Action mailed on Jan. 19, 2010, for U.S. Appl. No. 11/270,034, filed Nov. 8, 2005, 10 pages.
Non-Final Office Action mailed on Feb. 18, 2010, for U.S. Appl. No. 11/894,401, filed Aug. 20, 2007, 6 pages.
Non-Final Office Action mailed on Mar. 16, 2010, for U.S. Appl. No. 11/894,340, filed Aug. 20, 2007, 14 pages.
Non-Final Office Action mailed on Mar. 29, 2010, for U.S. Appl. No. 11/894,463, filed Aug. 20, 2007, 14 pages.
Non-Final Office Action mailed on Apr. 2, 2010, for U.S. Appl. No. 12/132,375, filed Jun. 3, 2008, 9 pages.
Non-Final Office Action mailed on Jun. 9, 2010, for U.S. Appl. No. 11/894,468, filed Aug. 20, 2007, 14 pages.
Non-Final Office Action mailed on Jun. 21, 2010, for U.S. Appl. No. 11/894,397, filed Aug. 20, 2007, 13 pages.
Non-Final Office Action mailed on Aug. 17, 2010, for U.S. Appl. No. 11/414,657, filed Apr. 27, 2006, 7 pages.
Non-Final Office Action mailed on Aug. 20, 2010, for U.S. Appl. No. 10/901,554, filed Jul. 27, 2004, 13 pages.
Non-Final Office Action mailed on Oct. 8, 2010, for U.S. Appl. No. 11/894,368, filed Aug. 20, 2007, 10 pages.
Non-Final Office Action mailed on Oct. 25, 2010, for U.S. Appl. No. 11/202,474, filed Aug. 11, 2005, 8 pages.
Non-Final Office Action mailed on Oct. 29, 2010, for U.S. Appl. No. 11/894,530, filed Aug. 20, 2007, 11 pages.
Non-Final Office Action mailed on Nov. 24, 2010, for U.S. Appl. No. 10/900,980, filed Jul. 27, 2004, 8 pages.
Non-Final Office Action mailed on Feb. 2, 2011, for U.S. Appl. No. 12/581,040, filed Oct. 16, 2009, 5 pages.
Non-Final Office Action mailed on Apr. 27, 2011, for U.S. Appl. No. 12/366,533, filed Feb. 5, 2009, 9 pages.
Non-Final Office Action mailed on Jul. 29, 2011, for U.S. Appl. No. 12/574,563, filed Oct. 6, 2009, 5 pages.
Non-Final Office Action mailed on Oct. 13, 2011, for U.S. Appl. No. 12/187,331, filed Aug. 6, 2008, 5 pages.
Non-Final Office Action mailed on Oct. 18, 2011, for U.S. Appl. No. 10/741,130, filed Dec. 19, 2003, 9 pages.
Non-Final Office Action mailed on Dec. 22, 2011, for U.S. Appl. No. 11/270,034, filed Nov. 8, 2005, 9 pages.
Notice of Allowance mailed on Aug. 4, 2009, for U.S. Appl. No. 10/901,555, filed Jul. 27, 2004, 7 pages.
Notice of Allowance mailed on Feb. 24, 2010, for U.S. Appl. No. 10/656,797, filed Sep. 4, 2003, 8 pages.
Notice of Allowance mailed on Apr. 28, 2010, for U.S. Appl. No. 10/901,019, filed Jul. 27, 2004, 7 pages.
Notice of Allowance mailed on Nov. 17, 2010, for U.S. Appl. No. 11/232,190, filed Sep. 20, 2005, 11 pages.
Notice of Allowance mailed on Dec. 6, 2010, for U.S. Appl. No. 12/132,375, filed Jun. 3, 2008, 9 pages.
Notice of Allowance mailed on Jul. 26, 2011, for U.S. Appl. No. 11/894,530, filed Aug. 20, 2007, 10 pages.
Final Office Action mailed on Mar. 19, 2012, for U.S. Appl. No. 12/574,563, filed Oct. 6, 2009, 6 pages.
Final Office Action mailed on Jun. 11, 2012, for U.S. Appl. No. 12/187,331, filed Aug. 6, 2008, 7 pages.
Non-Final Office Action mailed on Jun. 7, 2012, for U.S. Appl. No. 12/850,531, filed Aug. 4, 2010, 8 pages.
Notice of Allowance mailed on Jun. 11, 2012, for U.S. Appl. No. 10/741,130, filed Dec. 19, 2003.

* cited by examiner

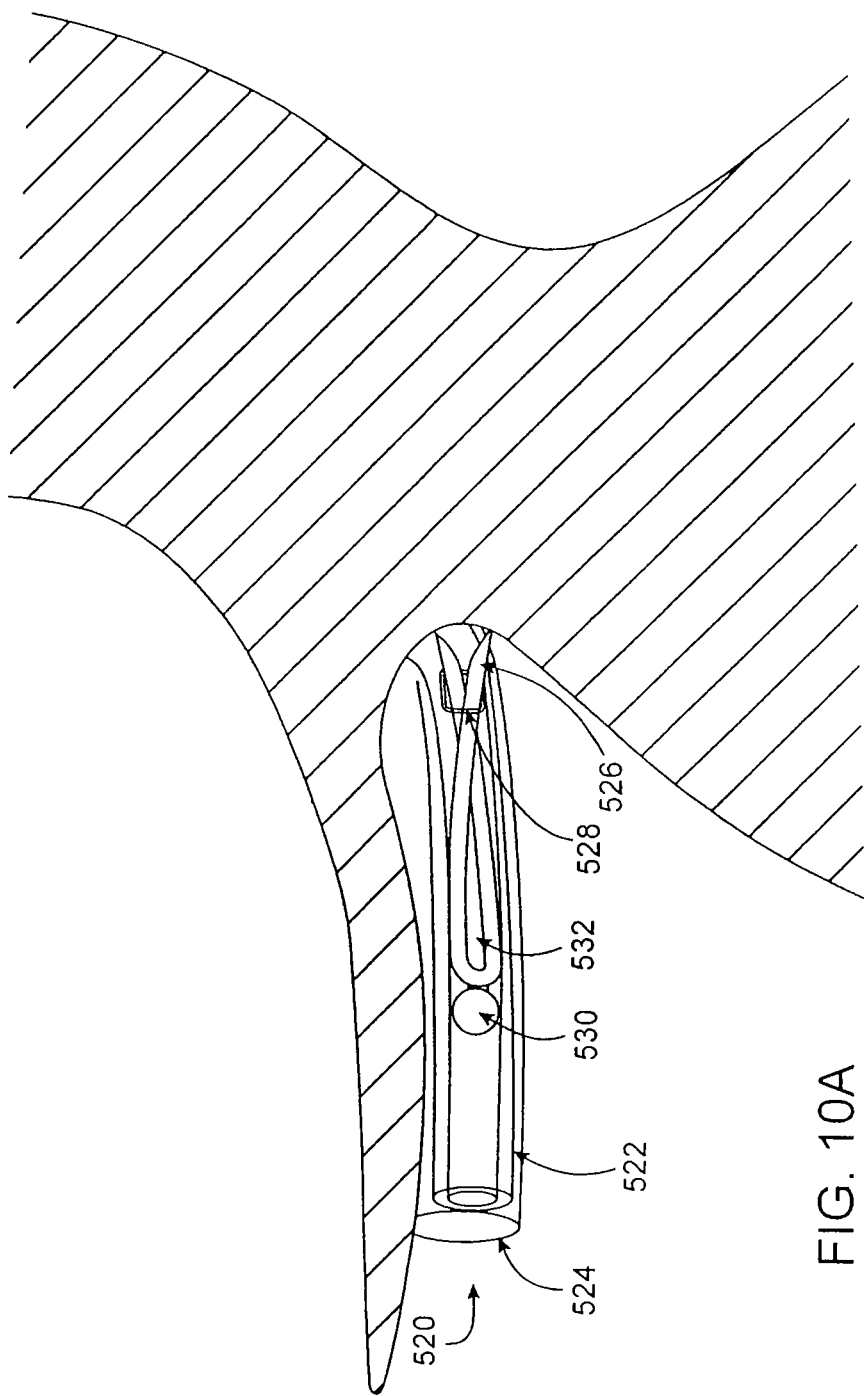

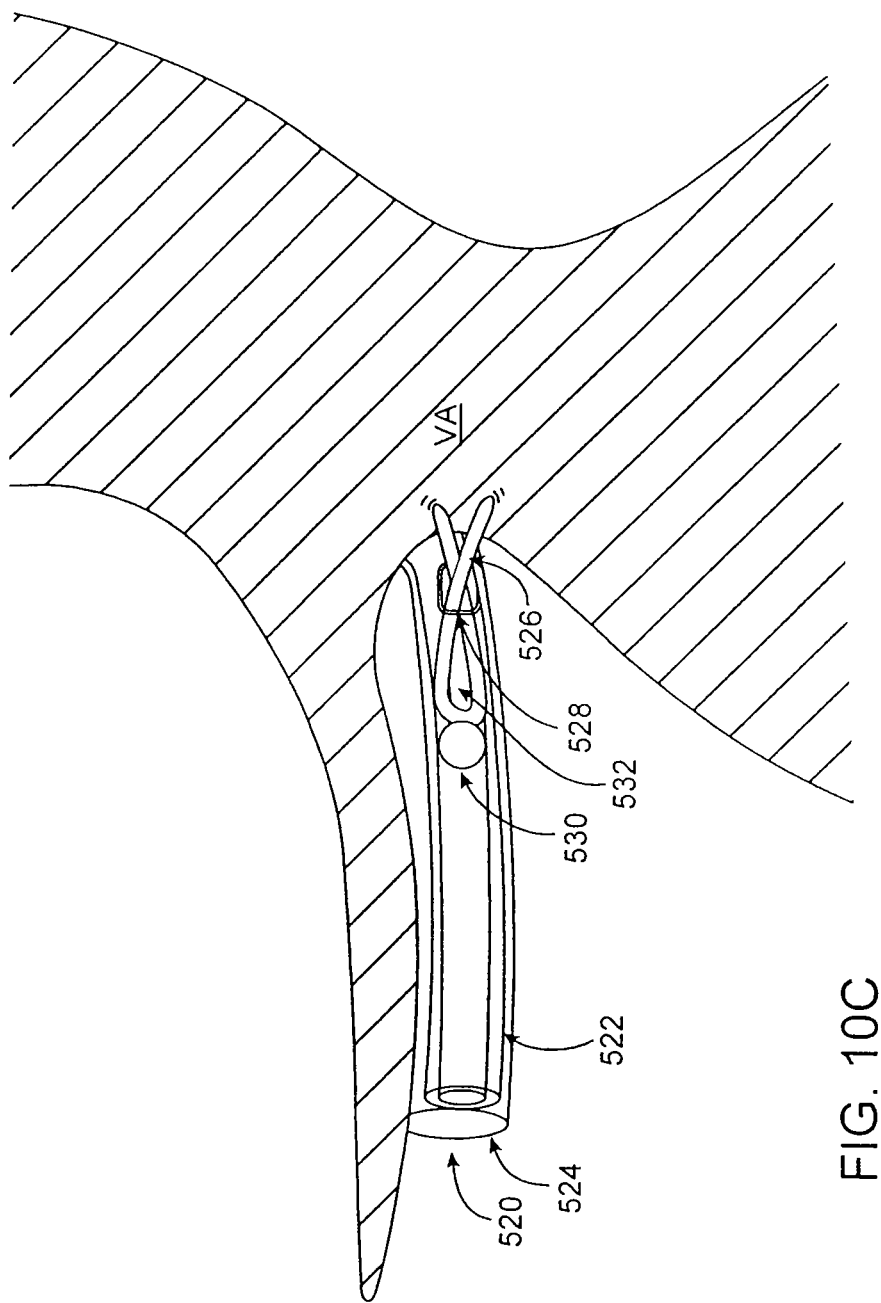

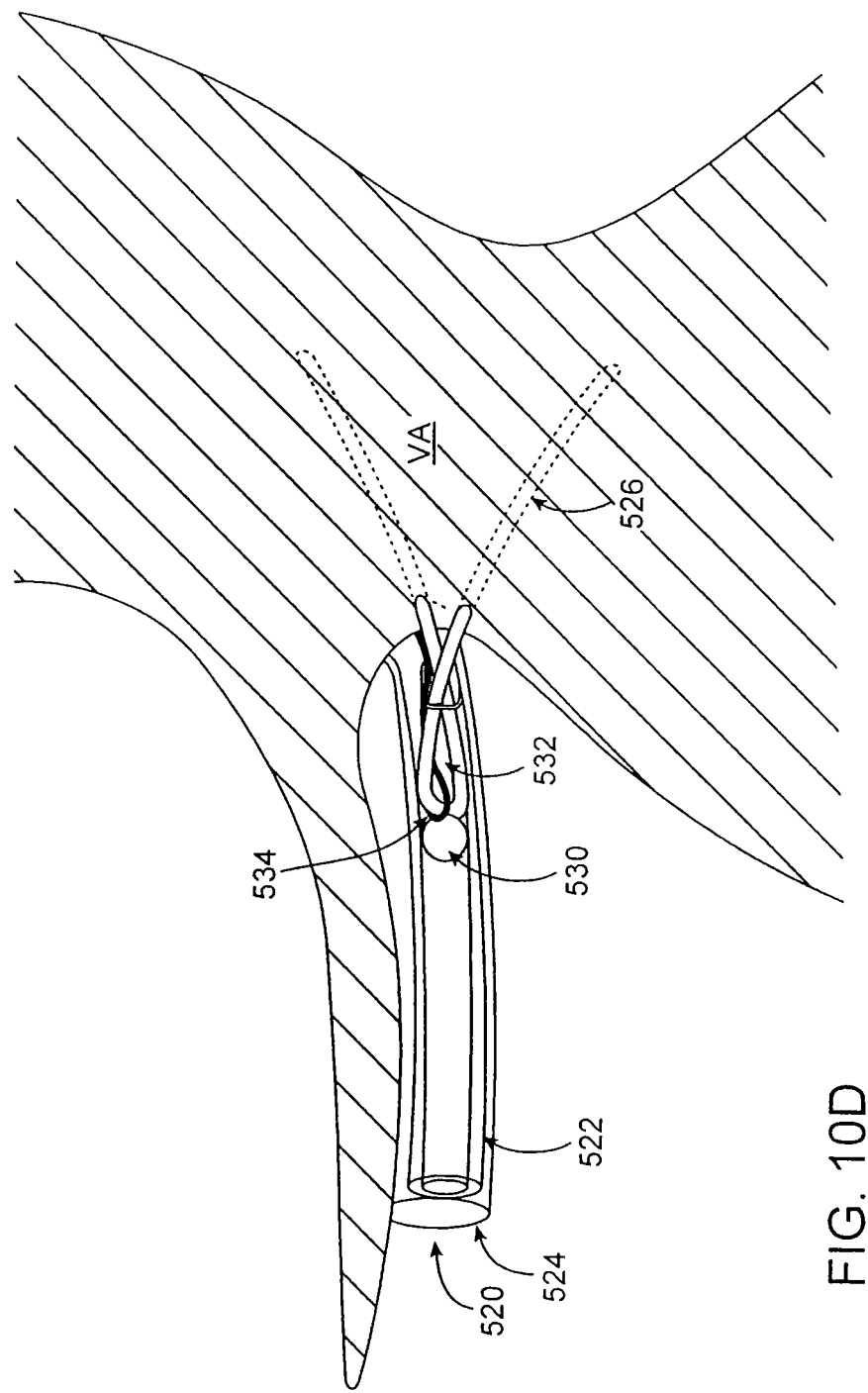

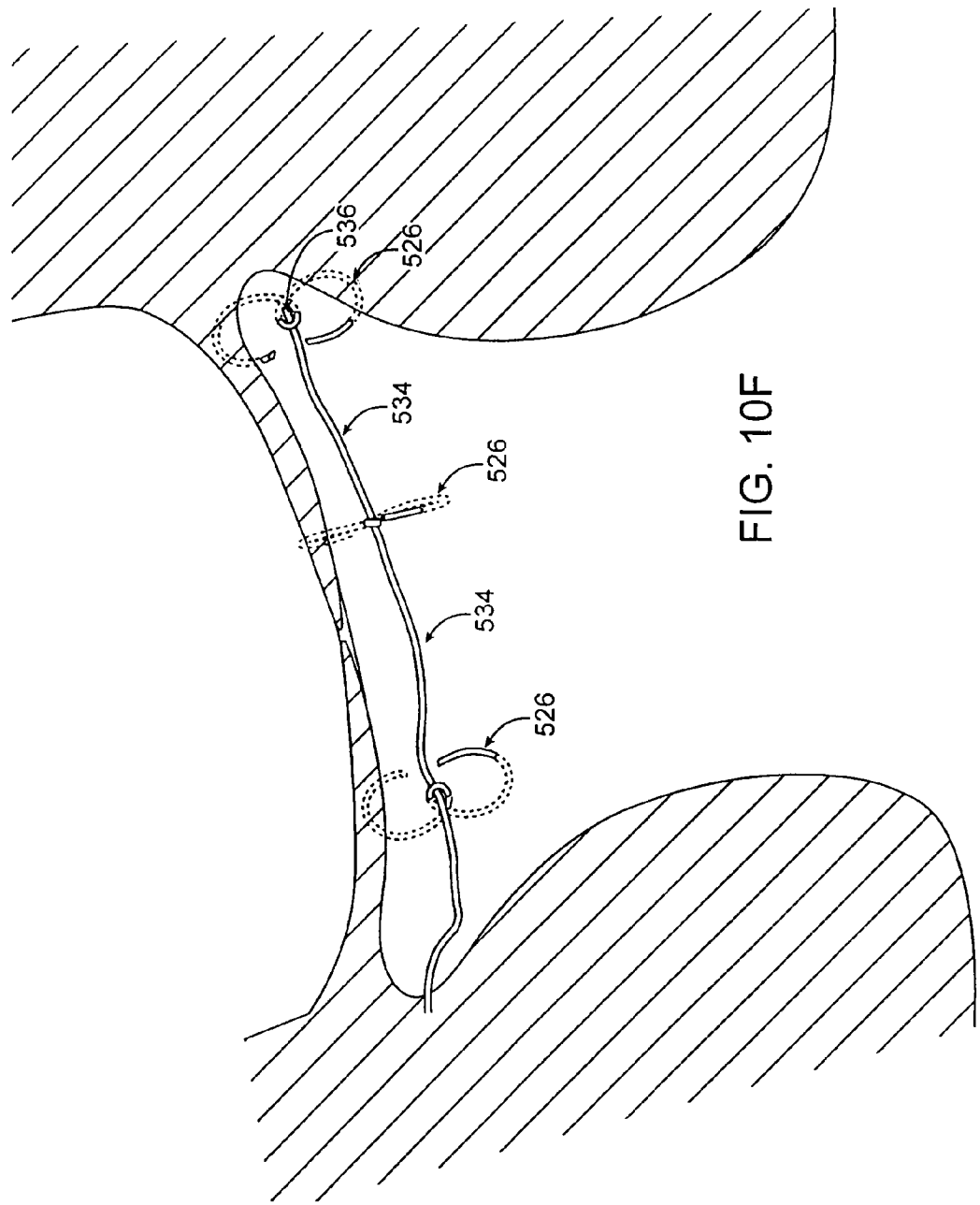

DEVICES AND METHODS FOR HEART VALVE REPAIR

CROSS REFERENCE TO RELATED APPLICATIONS

The present application is a divisional of U.S. patent application Ser. No. 10/741,130, filed on Dec. 19, 2003, now U.S. Pat. No. 8,287,555, which is a continuation-in-part of U.S. patent application Ser. No. 10/656,797, filed on Sep. 4, 2003, now U.S. Pat. No. 7,753,922, the full disclosure of which is incorporated herein by reference. The patent application Ser. No. 10/741,130 is also a continuation-in part of U.S. patent application Ser. No. 10/461,043 filed on Jun. 13, 2003, now U.S. Pat. No. 6,986,775, which claims the benefit of U.S. Provisional Application No. 60/388,935 filed on Jun. 13, 2002; U.S. Provisional Application No. 60/429,288, filed on Nov. 25, 2002; U.S. Provisional Application No. 60/445,890, filed on Feb. 6, 2003; and U.S. Provisional Application No. 60/462,502, filed on Apr. 10, 2003, the full disclosures of which are all incorporated herein by reference.

The present application also claims the benefit of U.S. Provisional Application No. 60/459,735, filed on Apr. 1, 2003; and U.S. Provisional Application No. 60/524,622, filed Nov. 24, 2003, the full disclosure of which are hereby incorporated by reference.

BACKGROUND OF THE INVENTION

1. Field of the Invention

The present invention relates generally to medical devices and methods. More particularly, the invention relates to devices and methods for enhancing cardiovascular valve repair, especially the repair of heart valves such as the mitral and tricuspid valves.

In recent years, many advances have been made to reduce the invasiveness of cardiac surgery. In an attempt to avoid open, stopped-heart procedures, which may be accompanied by high patient morbidity and mortality,: many devices and methods have been developed for operating on a heart through smaller incisions, operating on a beating heart, and even performing cardiac procedures via transvascular access. Different types of cardiac procedures, such as cardiac ablation techniques for treating atrial fibrillation, stenting procedures for atherosclerosis, and valve repair procedures for treating conditions such as mitral valve regurgitation have experienced significant technological advances. In implementing many minimally invasive cardiac surgery techniques, especially beating-heart techniques, one of the most significant challenges is positioning a treatment device (or multiple devices) in a desired location in or around the heart for performing the procedure. Another challenge, once a device is positioned, is to effectively deploy a given treatment into or on the target cardiac tissue.

One type of cardiac surgery which may benefit from less invasive techniques is heart valve repair. Traditional treatment of heart valve stenosis or regurgitation, such as mitral or tricuspid regurgitation, typically involves an open-heart surgical procedure to replace or repair the valve. Valve repair procedures typically involve annuloplasty, a set of techniques designed to restore the valve annulus shape and strengthen the annulus. Conventional annuloplasty surgery generally requires a large incision into the thorax of the patient (a thoracotomy), and sometimes a median sternotomy (cutting through the middle of the sternum). These open heart, open chest procedures routinely involve placing the patient on a cardiopulmonary bypass machine for sustained periods so that the patient's heart and lungs can be artificially stopped during the procedure. Finally, valve repair and replacement procedures are typically technically challenging and require a relatively large incision through the wall of the heart to access the valve.

Due to the highly invasive nature of open heart valve repair or replacement, many patients, such as elderly patients, patients having recently undergone other surgical procedures, patients with comorbid medical conditions, children, late-stage heart failure patients, and the like, are often considered too high-risk to undergo heart valve surgery and are relegated to progressive deterioration and cardiac enlargement. Often, such patients have no feasible alternative treatments for their heart valve conditions.

To obviate this situation, a number of devices and methods for repairing cardiac valves in a less invasive manner have been described. Some devices provide for heart valve repair through minimally invasive incisions or intravascularly, while others improve upon open heart surgical procedures on beating hearts, stopped hearts or both. As mentioned above, difficulties in performing minimally invasive intracardiac surgery include positioning a minimally invasive treatment device in a desired location for performing a procedure and effectively deploying a given treatment into or on the target cardiac tissue. In heart valve repair procedures, for example, it is often essential for a physician to secure one or more treatment devices to valve annulus tissue. Annular tissue tends to be more fibrous than surrounding muscular or valve leaflet tissue, thus providing a more suitable location for securing such treatment devices, such as anchors, to treat a heart valve. Positioning an anchor deliver device in a desired location adjacent the annular tissue may often be challenging, especially in an intravascular procedure when visualization of the location is limited.

Devices and methods that address these difficulties are described in U.S. Patent Application Nos. 60/445,890, 60/459,735, 60/462,502, 60/524,622, Ser. Nos. 10/461,043, and 10/656797, which were previously incorporated by reference. For example, these references describe devices and methods for exposing, stabilizing and/or performing a procedure on a heart valve annulus, such as a mitral valve annulus. Many of the devices and methods previously described by the inventors have been found to be highly effective, but improvements are still being sought.

Therefore, it would be beneficial to have improved devices and methods for performing a procedure on a heart valve annulus. Ideally, such devices could be conveniently positioned in a location for treatment of a valve annulus. Also ideally, such devices and methods would provide for enhanced delivery of treatment devices to a valve annulus, for example to enhance the securing of anchors to annular tissue. At least some of these objectives will be met by the present invention.

2. Description of the Background Art

Published U.S. Application 2002/0156526 describes a catheter-based method for performing annuloplasty. Published U.S. Application 2002/0042621 describes a heart valve annuloplasty system with constrictable plication bands which are optionally attached to a linkage strip. Published U.S. Application 2002/0087169 describes a remote controlled catheter system which can be used to deliver anchors and a tether for performing an annuloplasty procedure. Other patent publications of interest include WO01/26586; US2001/0005787; US2001/0014800; US2002/0013621; US2002/0029080; US2002/0035361; US2002/0042621; US2002/0095167; and US2003/0074012. U.S. Patents No. of interest include U.S. Pat. Nos. 4,014,492; 4,042,979; 4,043, 504; 4,055,861; 4,700,250; 5,366,479; 5,450,860; 5,571,215; 5,674,279; 5,709,695; 5,752,518; 5,848,969;5,860,992; 5,904,651; 5,961,539; 5,972,004; 6,165,183; 6,197,017; 6,250,308; 6,260,552; 6,283,993; 6,269,819; 6,312,447; 6,332,893; and 6,524,338. Publications of interest include De Simone et al. (1993) *Am. J. Cardiol.* 73:721-722, and Downing et al. (2001) *Heart Surgery Forum*, Abstract 7025. All of the above cited references are hereby incorporated by reference in the present application.

BRIEF SUMMARY OF THE INVENTION

Devices and methods of the present invention are generally used to facilitate transvascular, minimally invasive and other "less invasive" surgical procedures, by facilitating the delivery of treatment devices at a treatment site. "Less invasive," for the purposes of this application, means any procedure that is less invasive than traditional, large-incision, open surgical procedures. Thus, a less invasive procedure may be an open surgical procedure involving one or more relatively small incisions, a procedure performed via transvascular percutaneous access, a transvascular procedure via cut-down, a laparoscopic or other endoscopic procedure, or the like. Generally, any procedure in which a goal is to minimize or reduce invasiveness to the patient may be considered less invasive. Furthermore, although the terms "less invasive" and "minimally invasive" may sometimes be used interchangeably in this application, neither these nor terms used to describe a particular subset of surgical or other procedures should be interpreted to limit the scope of the invention. Generally, devices and methods of the invention may be used in performing or enhancing any suitable procedure.

The present application typically describes devices and methods for performing heart valve repair procedures, and more specifically heart valve annuloplasty procedures such as mitral valve annuloplasty to treat mitral regurgitation. Devices and methods of the invention, however, may be used in any suitable procedure, both cardiac and non-cardiac. For example, they may be used in procedures to repair any heart valve, to repair an atrial-septal defect, to access and possibly perform a valve repair or other procedure from (or through) the coronary sinus, to place one or more pacemaker leads, to perform a cardiac ablation procedure such as ablating around pulmonary veins to treat atrial fibrillation, and/or the like. In other embodiments, the devices and methods may be used to enhance a laparoscopic or other endoscopic procedure on any part of the body, such as the bladder, stomach, gastroesophageal junction, vasculature, gall bladder, or the like. Therefore, although the following description typically focuses on mitral valve and other heart valve repair, such description should not be interpreted to limit the scope of the invention as defined by the claims.

That being said, the present invention generally provides devices and methods for enhanced treatment of a cardiac valve annulus. Methods generally involve contacting an anchor delivery device with a length of a valve annulus, delivering a plurality of coupled anchors from the anchor delivery device to secure the anchors to the annulus, and drawing the anchors together to circumferentially tighten the annulus. Devices generally include an elongate catheter having a housing at or near the distal end for releasably housing a plurality of coupled anchors. Devices may be positioned such that the housing abuts or is close to valve annular tissue, such as at an intersection of the left ventricular wall and one or more mitral valve leaflets of the heart. Some embodiments include self-securing anchors, which may change from undeployed to deployed configurations. Anchors may be drawn together to tighten the annulus by cinching a tether slidably coupled with the anchors and/or by a self-deforming member coupled with the anchors.

In many cases, methods of the present invention will be performed on a beating heart. Access to the beating heart may be accomplished by any available technique, including intravascular, transthoracic, and the like. Intravascular access to a heart valve may be achieved using any suitable route or method. To perform a procedure on a mitral valve, for example, in one embodiment a catheter may be advanced through a femoral artery, to the aorta, and into the left ventricle of the heart, to contact a length of the mitral valve. Alternatively, access may be gained through the venous system, to a central vein, into the right atrium of the heart, and across the interatrial septum to the left side of the heart to contact a length of the mitral valve. In either of these two types of intravascular access, the catheter will often easily be advanced, once it enters the left side of the heart, into a space defined by the left ventricular wall, one or more mitral valve leaflets, and chordae tendineae of the left ventricle. This space provides a convenient conduit for further advancement of the catheter to a desired location for performing mitral valve repair. In alternative embodiments, a catheter device may access the coronary sinus and a valve procedure may be performed directly from the sinus. Furthermore, in addition to beating heart access, methods of the present invention may be used for intravascular stopped heart access as well as stopped heart open chest procedures. Any suitable intravascular or other access method is contemplated within the scope of the invention.

In one aspect of the invention, a method of constricting a valve annulus in a heart involves contacting an anchor delivery device with a length of the valve annulus, delivering a plurality of coupled anchors from the anchor delivery device to secure the anchors to the annulus, and drawing the anchors together to circumferentially tighten the valve annulus. In some embodiments, the anchors secure to the annulus by changing from an undeployed shape to a deployed shape upon their release from the anchor delivery device. Thus, the anchors may be called "self-securing," in that they secure to the tissue, at least in part, by changing from the undeployed shape to the deployed shape, and it is not required to crimp, drive or otherwise apply force to the anchors using the delivery device (although in some embodiments self-securing anchors may also be crimped, driven and/or the like.) In other embodiments, anchors non-self-securing anchors may be used, and such anchors may be secured to an annulus by driving, crimping and/or the like. "Anchors," which are described more fully below, are generally any devices that may be secured to a valve annulus.

In some embodiments, contacting the delivery device with the annulus comprises deforming a flexible distal portion of the anchor delivery device to conform the distal portion to the valve annulus. Deforming the distal portion may be performed by any suitable method, such as applying force to a tensioning cord, expanding a shaped expandable member coupled with the distal end, or the like. In some embodiments, for example, deforming the flexible distal portion comprises articulating the distal portion in at least two directions. For example, deforming the flexible distal portion may involve applying tension to a first tensioning cord to cause a first bend in the distal portion. Optionally, deforming the flexible distal portion may further involve applying tension to a second tensioning cord to cause a second bend in the distal portion. For example, the first bend may have approximately a C-shape to conform the distal portion to the annulus, and the second bend may be upwardly directed. In other embodiments, deforming the flexible distal portion may involve introducing air, a fluid, or the like into a shape-memory distal portion. Some embodiments may also include locking the shape of the flexible distal portion.

As mentioned previously, the contacting, delivering and drawing steps may be performed on any suitable heart valve, such as a mitral, tricuspid, aortic or pulmonary valve, as well as on other heart structures, such as a patent foramen ovale, or structures outside the heart, such as a gastroesophageal junction. For exemplary purposes only, devices and methods of the invention are often described below in the context of mitral valve repair for treatment of mitral regurgitation. In such mitral valve repair embodiments, as is also mentioned above, the method may optionally include advancing the flexible distal portion of an anchor delivery device within a space defined by the left ventricular wall, at least one mitral valve leaflet and at least one chordae tendineae of the left ventricle. It has been found that an elongate, flexible catheter may be conveniently passed under a mitral valve leaflet, into this subvalvular space, and advanced circumferentially around part or all of the circumference of the mitral valve. Tissue of the mitral valve annulus is typically located at a corner of this space defined by the intersection of the left ventricular wall and the inferior side of the mitral valve leaflet(s). Thus, passing a flexible distal portion of an elongate catheter into the subvalvular space may position the flexible distal portion in a desirable location for treating the valve annulus. For example, delivering anchors to contact and secure themselves to annular tissue is favorable to delivering the anchors to contact heart muscle or valve leaflet tissue, since annular tissue is more fibrous and thus more suitable for holding anchors, clips and the like. To further enhance contact of an anchor delivery device with a valve annulus the method may optionally include expanding an expandable member coupled with the delivery device within the treatment space to urge, wedge or press the delivery device further into the intersection of the left ventricular wall and the mitral valve leaflet(s).

In alternative embodiments, the anchor delivery device may be contacted with the valve annulus from within the left atrium of the heart. In some embodiments, a portion of the device may be contacted with the valve annulus from both the left atrium and the left ventricle. In such embodiments, the method may involve contacting the valve annulus with an anchor delivery device disposed in the left ventricle, contacting the valve annulus with a stabilizing member disposed in the left atrium, and delivering anchors from the anchor delivery device to contact and secure to the annulus. Stabilization devices and the combination of stabilization devices and anchor delivery devices are described more fully in U.S. patent application Ser. Nos. 10/461,043 and 10/656,797, which were previously incorporated by reference.

In some embodiments, delivering the plurality of tethered anchors may involve simply releasing the anchors from the delivery device. Alternatively, the anchors may be driven or otherwise forced from the delivery device. In some embodiments, delivering the plurality of tethered anchors comprises applying force to each of the anchors with an anchor contacting member. The anchor contacting member may be any suitable device disposed within the delivery device for contacting and applying force to the anchors and, thus, to force the anchors out of one or more openings in the delivery device. For example, a ball, plunger or other similar device coupled with a tether or "pull cord" may be disposed in a delivery device distal to a distal-most anchor. The ball may then be pulled or retracted proximally, relative to the delivery device, to sequentially contact the anchors and force each anchor out of the device. In an alternative embodiment, delivering the plurality of anchors may involve retracting at least one anchor retaining mandrel of the anchor delivery device to release the anchors. In some embodiments, for example, two mandrels are retracted, each mandrel positioned to retain an arm of each anchor. In another embodiment, one mandrel may be used, or any other suitable number of mandrels. In some embodiments, for example, each anchor has an opened arcuate undeployed shape and assumes a closed shape with overlapping ends after release from constraint. In such embodiments, two mandrels may be used, each mandrel retaining an "arm" of the opened arcuate shape.

Anchors, which may be any type of fastener devices, may have any suitable deployed and undeployed shapes and sizes, may be made from any suitable material(s), and the like. In some embodiments, the anchors are generally straight in their undeployed shape, so as to fit within a relatively narrow delivery catheter. Each anchor may have two sharpened tips and a small loop or similar shape between the tips, through which a tether may be passed. Upon deployment, the two sharpened tips may curve in opposite directions, to "bite" into and secure themselves to tissue. In various embodiments, the tips may continue to curve to any suitable degree—i.e., they may form semicircles, complete circles, overlapping helices, partial or complete ovoid shapes, or the like. In other embodiments, the undeployed shape may be approximately a C-shape or semicircle having two sharpened ends, and the deployed shape may be a closed circle in which the two ends overlap, wherein upon release from the delivery device the anchors secure to the annulus by penetrating the annulus with the ends and subsequently assuming the closed circle shape. These and other anchor embodiments typically have sharpened ends or tips to allow the anchors to secure to tissue. For example, the ends of an open C or semicircle bite into annular tissue, continue to close, and then overlap, so that the anchor is securely fastened to the tissue and no ends protrude. In some embodiments, such anchors will be flush with the surface of the tissue when deployed, so that no space exists between a portion of the anchor and the tissue.

In various embodiments, the tethered anchors may be released from the delivery device simultaneously or sequentially. For example, if a retractable anchor contacting member is used, it may contact one anchor at a time to force the anchors out sequentially. In other embodiments where one or more anchor retaining mandrels are used, the mandrel(s) may be retracted quickly enough in some embodiments so that the anchors are all released from the housing simultaneously. In another embodiment, the mandrel may be retracted more slowly, such that one anchor or several anchors at a time may be released and then subsequent anchors may subsequently be released. Some embodiments may further involve driving the anchors out of the delivery device using at least one expandable balloon member disposed within the delivery device. In alternative embodiments, a staple- or clip-driving device may be used. Although coupled anchors are typically used alone to tighten a valve annulus, in some embodiments coupled anchors may be used to secure a prosthesis to a heart valve annulus, such as an artificial valve, a Dacron cuff, any type of valve repair ring, or the like.

Drawing the anchors together to tighten the valve annulus may include, for example, cinching a tether extending through an eyelet on each of the plurality of anchors. Alternatively, a tether may be disposed between each of the plurality of anchors and the annulus, without the anchors having eyelets. In some embodiments, a self-deformiing coupling member extending between the anchors may be used instead of or in addition to a tether to constrict the annulus. For example, a self-deforming "backbone" made of super-elastic or shape-memory material such as Nitinol may be coupled with the anchors, such that when the tethered anchors and the backbone are released to allow the anchors to secure to the annular tissue, the backbone constricts to bring the anchors closer together and thus constrict the annulus. In one embodiment, such a backbone is shaped generally as a straight or curved line before deployment and assumes a configuration having multiple bends after deployment. The multiple bends reduce the overall length of the backbone, thus acting to cinch the anchors to constrict the annulus. In some embodiments, a tether and a self-deforming coupling member may be used together to tighten the valve annulus, and the tether and the coupling member may optionally be coupled together.

In embodiments in which the anchors are slidably tethered, the method typically further includes cinching the tether, fixing the tether to at least a terminal anchor of the plurality of anchors, and cutting the tether to leave the cinched anchors in place, coupled with the valve annulus. Any or all of these steps may optionally be performed using a "termination device," such as a termination catheter or sheath that is advanced over the tether to a location near the terminal anchor. The terminal anchor is typically the last anchor placed in the length of the valve annulus, which may be the most proximal anchor relative to the oter anchors. A termination catheter, for example, may be used to apply oppositely-directed force while the tether is cinched. It may also house an adhesive device, such as a Nitinol knot positioned over the tether, for securing the tether to the terminal anchor. Once the tether is cinched and attached to the terminal anchor, a cutting device, such as a guillotine, coupled with the termination catheter may be used to cut the tether proximal to the terminal anchor to leave the cinched anchors behind, secured to the valve annulus. Alternatively, any other suitable methods and devices may be used to provide cinching, attaching and/or cutting of a tether.

In some embodiments, a number of anchors may be applied to a first length of a valve annulus to tighten that length of the annulus, and then a number of additional anchors may be applied to a second length of the annulus to tighten that length. Such a method may actually be more convenient, in some instances, than contacting a delivery device with a larger portion of the circumference of the annulus and applying and cinching all the anchors. For example, in one embodiment a delivery device is contacted with an anterior length of the valve annulus, anchors are released to contact and tighten the annulus, and then the delivery device is contacted with a posterior length of the annulus and additional anchors are released to contact and tighten the posterior length.

In some embodiments, the method may also include stabilizing the annulus with the delivery device prior to releasing the anchors. Annulus stabilizing devices and methods are described in more detail, for example, in U.S. patent application Ser. Nos. 10/461,043 and 10/656,797, which were previously incorporated by reference.

Methods may also optionally include visualizing the valve annulus. Visualization devices and methods are described more fully in U.S. Provisional Patent Application Ser. No. 60/500,773, filed on Sep. 3, 2003, the full disclosure of which is hereby incorporated by reference. In some embodiments, for example, visualizing is performed using at least one visualization device such as an ultrasound device, an angioscopic device, a transesophageal echocardiogram device and a fluoroscopic device. In one embodiment, the ultrasound device comprises a gel-containing cone for enhancing ultrasound visualization. In one embodiment, visualizing comprises using a real-time Doppler ultrasound device to visualize a regurgitant flow across the heart valve during at least the cinching step. In some embodiments, the method may further include visualizing a reduction in the regurgitant flow during the cinching step and selecting an amount of cinching based on the reduction in the regurgitant flow. In some embodiments, the visualization device is coupled with the anchor delivery device. For example, the visualization device may comprise an angioscope having a viewing end within or adjacent to a lens, bubble or inflatable balloon which displaces blood to permit viewing in the beating heart.

In another aspect of the invention, a method of constricting a valve annulus in a heart involves: contacting an anchor delivery device having a cross-sectional diameter of about 1.67 mm or less with a length of the valve annulus; delivering a plurality of coupled anchors from the anchor delivery device to secure the anchors to the annulus, each anchor having a deployed shape with a radius of at least about 3 mm; and drawing the anchors together to circumferentially tighten the valve annulus. It has been found that anchors may be disposed in and delivered from a delivery device in such a way as to allow relatively large-radius anchors to be delivered from a relatively small-diameter delivery device. Anywhere from one anchor to 20 anchors may be delivered in some embodiments, although the invention is not limited to such numbers. In one embodiment, for example, at least 10 anchors, each having a deployed radius of about 3 mm or more, may be delivered from a delivery device having a cross-sectional diameter of about 1.67 mm or less.

In another aspect of the present invention, a device for applying coupled anchors to an annulus of a heart valve comprises: an elongate shaft having a proximal end and a distal end; a housing adjacent the distal end; a plurality of coupled anchors disposed within the housing; at least one anchor contacting member for causing the anchors to be delivered from the housing; and at least one actuator at or near the proximal end of the shaft for affecting the anchor contacting member to cause delivery of the anchors to the valve annulus.

In some embodiments, the elongate shaft comprises a flexible catheter which is advancable intravascularly to the heart. In a preferred embodiment, a flexible elongate shaft has a diameter of about 5 French (1.67 mm) or less and deploys anchors having a radius, when deployed, of about 3 mm or more. The housing itself may house any suitable number of anchors. In one embodiment, for example, the housing holds between 1 anchor and 20 anchors, and more preferably about 3-10 anchors, and in one embodiment 10 anchors. Also in some embodiments, the housing is sufficiently flexible to allow the housing to conform to the annulus. For example, the housing may conform to the annulus at an intersection of a left ventricular wall and one or more mitral valve leaflets of the heart. The housing may thus be positioned or advanced through the subvalvular space as discussed above. In some embodiments, the housing is coupled with an actuator for deforming the housing to conform it to the annulus. The housing may have any suitable configuration, but in some embodiments it has a cross section with a shape that is roughly semi-circular, circular, oval, part of an oval, a partial or complete ellipse, or the like. For example, a housing with an elliptical shape may sometimes be used to help ensure that an anchor delivering surface of the housing comes into contact with the annular tissue. In various embodiments, the housing may have one or multiple openings for allowing egress of the anchors. In one embodiment, for example, the housing has multiple openings, each opening suitable for egress of one anchor.

In some embodiments, the housing includes a shape-changing portion, typically a distal portion. Such embodiments may further include a first tensioning cord coupled with the shape-changing portion for applying tension to the shape-changing portion to cause it to bend in at least a first direction. Optionally, a second tensioning cord may be coupled with the shape-changing portion for applying tension to the shape-changing portion to cause it to bend in at least a second direction. The first direction, for example, may be approximately a C-shape for conforming to the annulus and the second direction comprises an upward or proximal direction for applying force to the annulus. In some embodiments, the shape-changing portion includes multiple notches along at least one side to control bending into a curve which conforms to the shape of the annulus. Alternatively, the shape-changing portion may comprise multiple stacked segments coupled with at least the first tensioning member to control bending into the shape of the annulus. In other embodiments, the shape-changing portion comprises a shape-memory material configured to conform to the shape of the annulus. In some embodiments, the shape-changing portion further comprises at least one lumen for introducing a fluid to cause the shape-memory material to conform to the shape of the annulus. The distal portion of the housing may alternatively be coupled with a shaped expandable balloon for deforming the distal portion. In some embodiments, the housing may be coupled with an expandable member such that when the expandable member expands, it helps wedge, drive or press the housing against valve annulus tissue. For example, such an expandable member may help to wedge a housing into the corner formed by a ventricular wall and a valve leaflet.

As explained above, anchors of the device may have any suitable shape, size and properties and may be made of any suitable materials. Anchors may be self-deforming in some embodiments, thus having an undeployed shape when constrained in the housing of the delivery device and assuming a deployed shape after release from the housing. In one embodiment, each of the plurality of coupled anchors has a generally straight configuration, with two sharpened tips and a loop between the two. Upon deployment, such an anchor may curve, with each tip curving in an opposite direction to bite into tissue. The loop, in turn, may act as an eye for a tether. In another embodiment, each anchor may have a C-shaped or semicircular undeployed shape and an overlapping circle or key ring deployed shape. In such an embodiment, the open ends of the C are typically sharpened, to enable the anchor to enter tissue of a valve annulus. As the C-shaped anchor contacts and enters the tissue, it also closes, and the ends overlap to form a circle or key-ring-shaped deployed anchor. Such an anchor may be applied such that it rests flush with the surface of the annular tissue without protruding sharp ends or other parts. The anchors may be made of Nitinol, shape-memory stainless steel, or any other super-elastic or shape-memory material. Alternatively, the anchors may be spring loaded or otherwise housed within the housing so as to change from an undeployed to a deployed shape upon release from the housing.

In some embodiments, the anchors are slidably coupled with a tether. In such embodiments, each of the plurality of anchors may include at least one eyelet, with the tether slidably passing through the eyelet of each anchor. Alternatively, the tether may extend along the anchors to be positioned between the anchors and annular tissue upon deployment. In other embodiments, the anchors may be coupled by a self-deforming coupling member fixedly coupled with each anchor. For example, the coupling member (or "backbone") may comprise a Nitinol member having an undeployed shape approximating a straight line and a deployed shape of a line having multiple bends. Upon changing from the undeployed shaped to the deployed shape, the coupling member may cinch the anchors to circumferentially tighten the valve annulus. Some embodiments may include both a tether and a self-deforming coupling member, with both being available to provide cinching of a valve annulus.

In some embodiments, the at least one anchor contacting member comprises at least one retractable force applying device which, when retracted proximally relative to the housing, sequentially contacts the anchors to apply force to the anchors such that they exit the housing via at least one opening in the housing. Such a force applying device, for example, may comprise a ball, plate, anchor, hook, plunger or the like, coupled with a cord, wire, tether or the like. When the tether is pulled proximally, the ball contacts the distal-most anchor in the delivery device and forces it out an opening in the device. When retracted further, the ball then contacts the next anchor, forcing it out, and so on. In alternative embodiments, the at least one anchor contacting member comprises at least one movable retaining member. For example, such a movable retaining member may comprise one or more anchor retaining mandrels, slidably disposed in the housing so that retracting the mandrel(s) releases one or more of the anchors. Sometimes, for example, two mandrels are positioned in the housing to retain two arms of each anchor, for example when the undeployed shape of each anchor is approximately a C-shape or semicircle. The mandrel (or mandrels) may typically be retracted to release anchors one at a time, in groups, or all at once.

In some embodiments, the at least one actuator includes means for cinching the coupled anchors to reduce the circumference of the valve annulus. Such an actuator may comprise, for example, a trigger, a handle, a plunger, a squeeze-activated device, a syringe-grip device, a foot-operated device, or the like. Some embodiments of the device also include at least one expandable member disposed within the housing for pushing the anchors out of the housing.

In yet another aspect of the invention, a device for applying multiple tethered anchors to an annulus of a heart valve comprises: a flexible elongate catheter having a distal portion for delivering the tethered anchors, the distal portion having a cross-sectional diameter of about 1.67 mm or less; a plurality of tethered anchors disposed within the distal portion, each anchor having a radius of at least about 3 mm when deployed from the housing; and at least one anchor delivery member coupled with the catheter for causing the anchors to be delivered from the catheter.

In another aspect of the invention, a self-securing anchor for attaching to annular tissue of a heart valve comprises a super-elastic or shape-memory material having a relatively elongate undeployed shape allowing the anchor to be disposed within a delivery catheter having a cross-sectional diameter of 1.67 mm or less, and assuming a deployed shape with a radius of at least 3 mm upon its release from the delivery device. Generally, such an anchor may have two sharpened tips of the anchor curve in opposite directions when the anchor is released from the delivery device. Optionally, the anchor may include an eyelet disposed between the two sharpened tips.

In still another aspect of the present invention, a self-securing anchor for attaching to annular tissue of a heart valve comprises a shape-memory material having an opened arcuate undeployed shape and assuming a closed shape with overlapping ends after release from constraint. The undeployed and deployed shapes may be any suitable shapes. In one embodiment, for example, the undeployed shape is approximately a C-shape or semicircle having two sharpened ends, and the deployed shape is a closed circle in which the two ends overlap. In some embodiments, the anchor is configured to lie flush with the annular tissue when secured to the tissue. Any super-elastic or shape-memory material may be used to form the anchor, such as Nitinol or any other suitable material.

These and other embodiments are described more fully below with reference to the drawing figures.

BRIEF DESCRIPTION OF THE DRAWINGS

FIGS. 10A-10F demonstrate a method for applying anchors to a valve annulus and cinching the anchors to tighten the annulus, using an anchor delivery device according to an embodiment of the invention.

DETAILED DESCRIPTION OF THE INVENTION

Devices and methods of the present invention are generally used to facilitate transvascular, minimally invasive and other "less invasive" surgical procedures, by facilitating the delivery of treatment devices at a treatment site. Although the following description focuses on use of devices and methods of the invention for mitral valve repair, the devices and methods may be used in any suitable procedure, both cardiac and non-cardiac. When used for treatment of a cardiac valve annulus, the inventive methods generally involve contacting an anchor delivery device with a length of the valve annulus, delivering a plurality of coupled anchors from the anchor delivery device, and drawing the anchors together to tighten the annulus. Devices generally include an elongate catheter having a housing at or near the distal end for releasably housing a plurality of coupled anchors. Devices may be positioned such that the housing abuts or is close to valve annular tissue, such as in a location within the left ventricle defined by the left ventricular wall, a mitral valve leaflet and chordae tendineae. Self-securing anchors having any of a number of different configurations may be used in some embodiments.

In many cases, methods of the present invention will be performed on a beating heart. Access to the beating heart may be accomplished by any available technique, including intravascular, transthoracic, and the like. In addition to beating heart access, the methods of the present invention may be used for intravascular stopped heart access as well as stopped heart open chest procedures.

Figure 1:
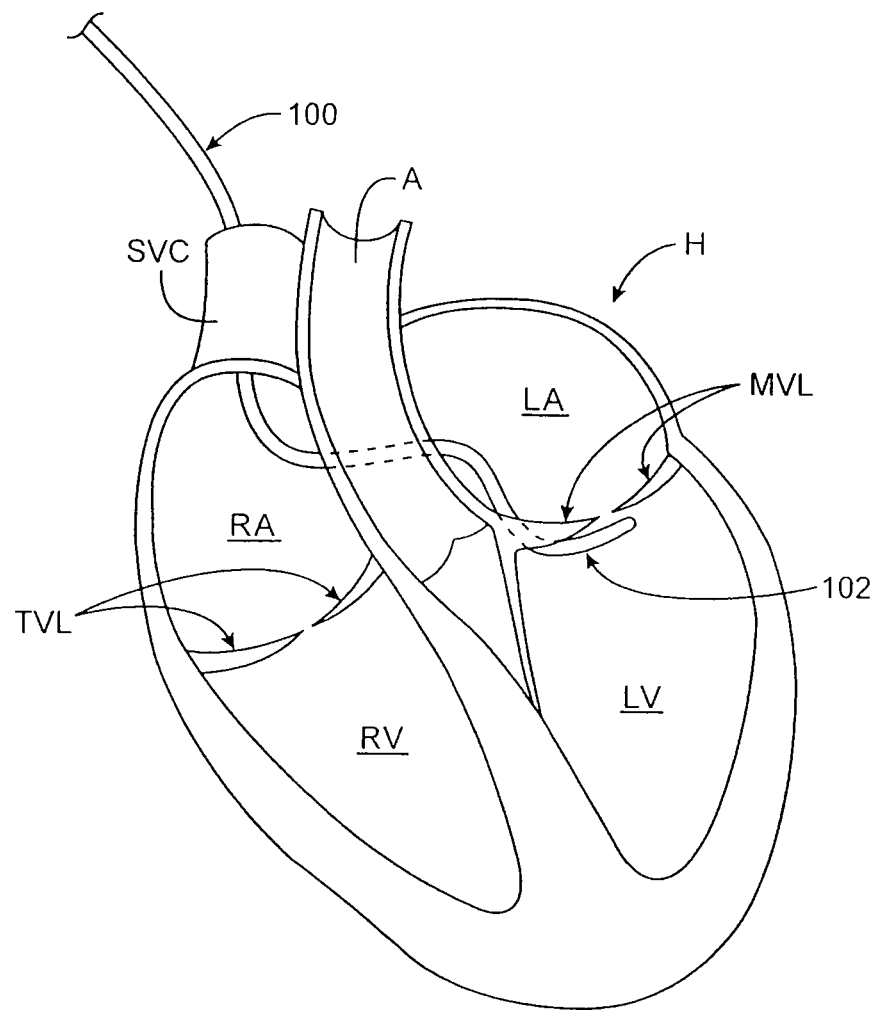
FIG. 1 is a cross-sectional view of a heart with a flexible anchor delivery device being positioned for treatment of a mitral valve annulus, according to one embodiment of the present invention.

Referring now to FIG. 1, a heart H is shown in cross section, with an elongate anchor delivery device 100 introduced within the heart H. Generally, delivery device 100 comprises an elongate body with a distal portion 102 configured to deliver anchors to a heart valve annulus. (In FIGS. 1, 2A and 2B, distal portion 102 is shown diagrammatically without anchors or anchor-delivery mechanism to enhance clarity of the figures.) In some embodiments, the elongate body comprises a rigid shaft, while in other embodiments it comprises a flexible catheter, so that distal portion 102 may be positioned in the heart H and under one or more valve leaflets to engage a valve annulus via a transvascular approach. Transvascular access may be gained, for example, through the internal jugular vein (not shown) to the superior vena cava SVC to the right atrium RA, across the interatrial septum to the left atrium LA, and then under one or more mitral valve leaflets MVL to a position within the left ventricle (LV) under the valve annulus (not shown). Alternatively, access to the heart may be achieved via the femoral vein and the inferior vena cava. In other embodiments, access may be gained via the coronary sinus (not shown) and through the atrial wall into the left atrium. In still other embodiments, access may be achieved via a femoral artery and the aorta, into the left ventricle, and under the mitral valve. Any other suitable access route is also contemplated within the scope of the present invention.

In other embodiments, access to the heart H may be transthoracic, with delivery device 100 being introduced into the heart via an incision or port on the heart wall. Even open heart surgical procedures may benefit from methods and devices of the invention. Furthermore, some embodiments may be used to enhance procedures on the tricuspid valve annulus, adjacent the tricuspid valve leaflets TVL, or any other cardiac or vascular valve. Therefore, although the following description typically focuses on minimally invasive or less invasive mitral valve repair for treating mitral regurgitation, the invention is in no way limited to that use.

Figure 2A:
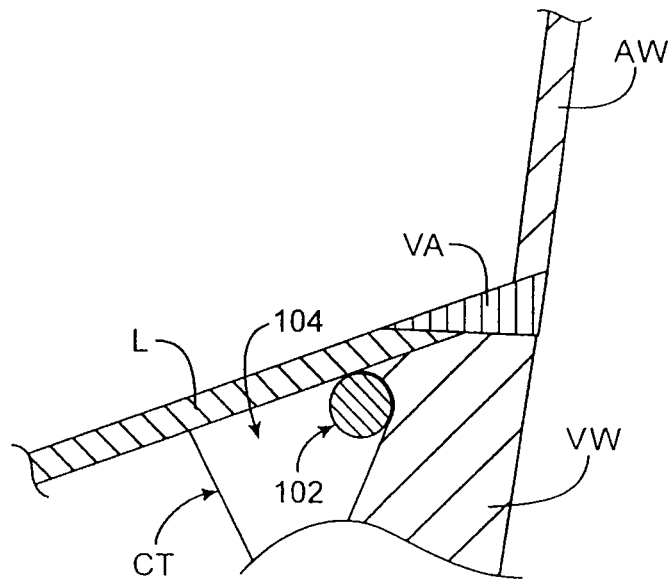
FIGS. 2A and 2B are cross-sectional views of a portion of a heart, schematically showing positioning of a flexible device for treatment of a mitral valve annulus, according to one embodiment of the present invention.
Figure 2B:
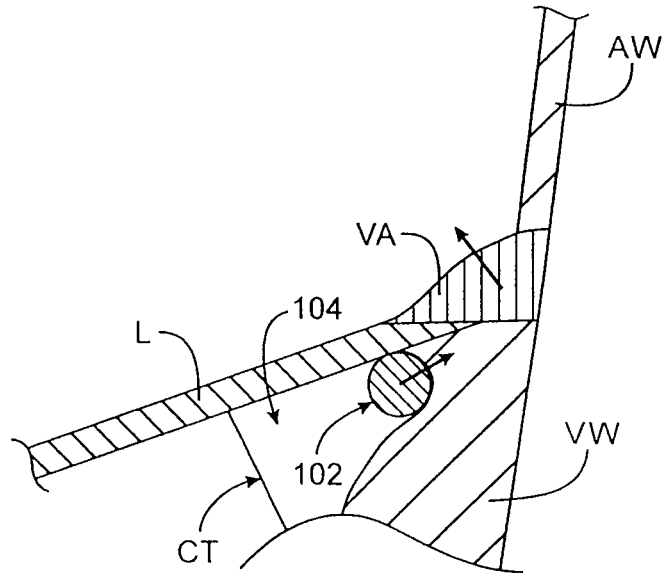

With reference now to FIGS. 2A and 2B, a method for positioning delivery device 100 for treating a mitral valve annulus VA is depicted diagrammatically in a cross-sectional view. First, as in FIG. 2A, distal portion 102 is positioned in a desired location under a mitral valve leaflet L and adjacent a ventricular wall VW. (Again, distal portion 102 is shown without anchors or anchor-delivery mechanism for demonstrative purposes.) The valve annulus VA generally comprises an area of heart wall tissue at the junction of the ventricular wall VW and the atrial wall AW that is relatively fibrous and, thus, significantly stronger that leaflet tissue and other heart wall tissue.

Distal portion 102 may be advanced into position under the valve annulus by any suitable technique, some of which are described below in further detail. Generally, distal portion 102 may be used to deliver anchors to the valve annulus, to stabilize and/or expose the annulus, or both. In one embodiment, using a delivery device having a flexible elongate body as shown in FIG. 1, a flexible distal portion 102 may be passed from the right atrium RA through the interatrial septum in the area of the foramen ovale (not shown—behind the aorta A), into the left atrium LA and thus the left ventricle LV. Alternatively, flexible distal portion 102 may be advanced through the aorta A and into the left ventricle LV, for example using access through a femoral artery. Oftentimes, distal portion 102 will then naturally travel, upon further advancement, under the posterior valve leaflet L into a space defined above a subvalvular space 104 roughly defined for the purposes of this application as a space bordered by the inner surface of the left ventricular wall VW, the inferior surface of mitral valve leaflets L, and cordae tendineae CT connected to the ventricular wall VW and the leaflet L. It has been found that a flexible anchor delivery catheter, such as the delivery devices of the present invention, when passed under the mitral valve via an intravascular approach, often enters subvalvular space 104 relatively easily and may be advanced along space 104 either partially or completely around the circumference of the valve. Once in space 104, distal portion 102 may be conveniently positioned at the intersection of the valve leaflet(s) and the ventricular wall VW, which intersection is immediately adjacent or very near to the valve annulus VA, as shown in FIG. 2A. These are but examples of possible access routes of an anchor delivery device to a valve annulus, and any other access routes may be used.

In some embodiments, distal portion 102 includes a shape-changing portion which enables distal portion 102 to conform to the shape of the valve annulus VA. The catheter may be introduced through the vasculature with the shape-changing distal portion in a generally straight, flexible configuration. Once it is in place beneath the leaflet at the intersection between the leaflet and the interior ventricular wall, the shape of distal portion 102 is changed to conform to the annulus and usually the shape is "locked" to provide sufficient stiffness or rigidity to permit the application of force from distal portion 102 to the annulus. Shaping and optionally locking distal portion 102 may be accomplished in any of a number of ways. For example, in some embodiments, a shape-changing portion may be sectioned, notched, slotted or segmented and one of more tensioning cords, wires or other tensioning devices coupled with the shape-changing portion may be used to shape and rigidify distal portion 102. A segmented distal portion, for example, may include multiple segments coupled with two tensioning cords, each cord providing a different direction of articulation to the distal portion. A first bend may be created by tensioning a first cord to give the distal portion a C-shape or similar shape to conform to the valve annulus, while a second bend may be created by tensioning a second cord to articulate the C-shaped member upwards against the annulus. In another embodiment, a shaped expandable member, such as a balloon, may be coupled with distal portion 102 to provide for shape changing/deforming. In various embodiments, any configurations and combinations may be used to give distal portion 102 a desired shape.

In transthoracic and other embodiments, distal portion 102 may be pre-shaped, and the method may simply involve introducing distal portion 102 under the valve leaflets. The pre-shaped distal portion 102 may be rigid or formed from any suitable super-elastic or shape memory material, such as nitinol, spring stainless steel, or the like.

In addition to delivering anchors to the valve annulus VA, delivery device 100 (and specifically distal portion 102) may be used to stabilize and/or expose the valve annulus VA. Such stabilization and exposure are described fully in U.S. patent application Ser. No. 10/656,797, which was previously incorporated by reference. For example, once distal portion 102 is positioned under the annulus, force may be applied to distal portion 102 to stabilize the valve annulus VA, as shown in FIG. 2B. Such force may be directed in any suitable direction to expose, position and/or stabilize the annulus. For example, upward and lateral force is shown in FIG. 2B by the solid-headed arrow drawn from the center of distal portion 102. In other cases, only upward, only lateral, or any other suitable force(s) may be applied. With application of force to distal portion 102, the valve annulus VA is caused to rise or project outwardly, thus exposing the annulus for easier viewing and access. The applied force may also stabilize the valve annulus VA, also facilitating surgical procedures and visualization.

Some embodiments may include a stabilization component as well as an anchor delivery component. For example, some embodiments may include two flexible members, one for contacting the atrial side of a valve annulus and the other for contacting the ventricular side. In some embodiments, such flexible members may be used to "clamp" the annulus between them. One of such members may be an anchor delivery member and the other may be a stabilization member, for example. Any combination and configuration of stabilization and/or anchor delivery members is contemplated.

Figure 2C:
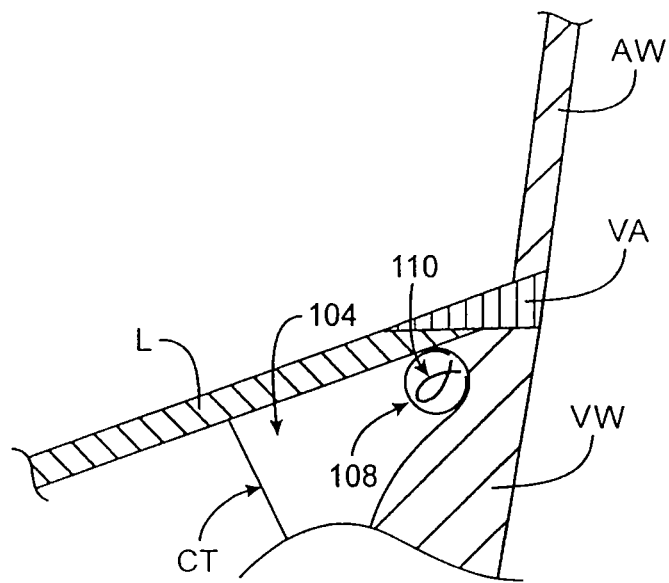
FIGS. 2C and 2D are cross-sectional views of a portion of a heart, showing positioning of a flexible anchor delivery device for treatment of a mitral valve annulus, according to one embodiment of the present invention.
Figure 2D:
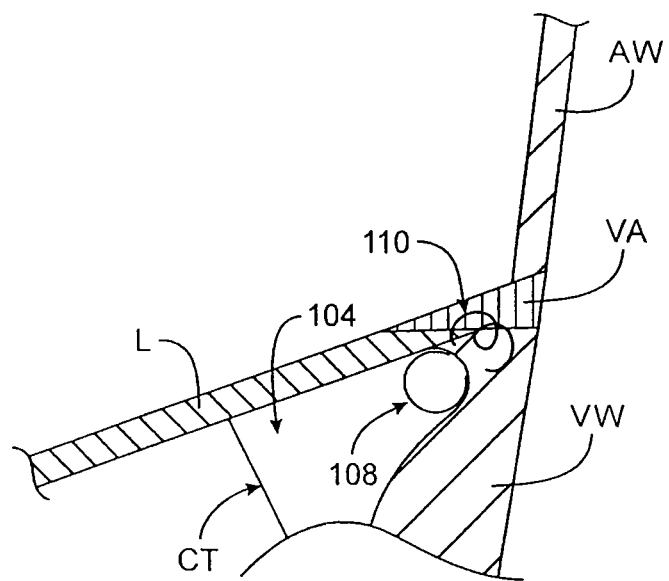

Referring now to FIGS. 2C and 2D, an anchor delivery device 108 is shown delivering an anchor 110 to a valve annulus VA. Of course, these are again representational figures and are not drawn to scale. Anchor 110 is shown first housed within delivery device 108 (FIG. 2C) and then delivered to the annulus VA (FIG. 2D). As is shown, in one embodiment anchors 110 may have a relatively straight configuration when housed in delivery device 108, perhaps with two sharpened tips and a loop in between the tips. Upon deployment from delivery device 108, the tips of anchor 110 may curve in opposite directions to form two semi-circles, circles, ovals, overlapping helices or the like. This is but one example of a type of self-securing anchor which may be delivered to a valve annulus. Typically, multiple coupled anchors 110 are delivered, and the anchors 110 are drawn together to tighten the valve annulus. Methods for anchor delivery and for drawing anchors together are described further below.

Although delivery device 108 is shown having a circular cross-sectional shape in FIGS. 2C and 2D, it may alternatively have any other suitable shape. In one embodiment, for example, it may be advantageous to provide a delivery device having an ovoid or elliptical cross-sectional shape. Such a shape may help ensure that the device is aligned, when positioned between in a corner formed by a ventricular wall and a valve leaflet, such that one or more openings in the delivery device is oriented to deliver the anchors into valve annulus tissue. To further enhance contacting of the valve annulus and/or orientation of the delivery device, some embodiments may further include an expandable member, coupled with the delivery device, which expands to urge or press or wedge the delivery device into the corner formed by the ventricle wall and the leaflet to contact the valve annulus. Such enhancements are described further below.

Figure 3:
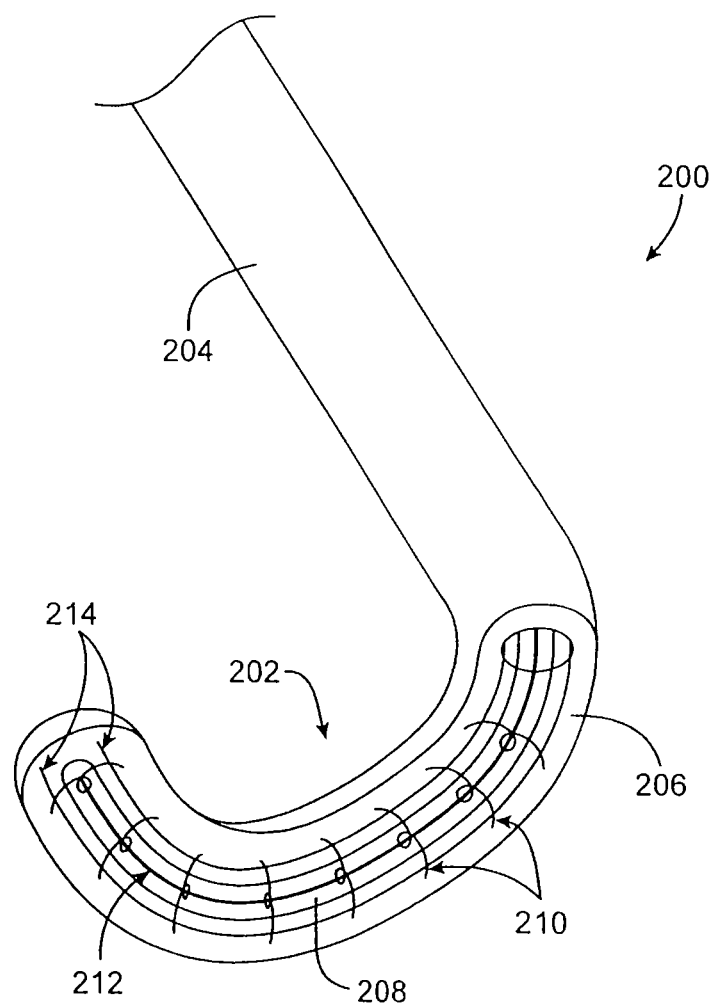
FIG. 3 is a perspective view of a distal portion of an anchor delivery device, according to one embodiment of the invention.

With reference now to FIG. 3, one embodiment of a portion of an anchor delivery device 200 suitably includes an elongate shaft 204 having a distal portion 202 configured to deliver a plurality of anchors 210, coupled with a tether 212, to tissue of a valve annulus. Tethered anchors 210 are housed within a housing 206 of distal portion 202, along with one or more anchor retaining mandrels 214 and an expandable member 208. Many variations may be made to one or more of these features, and various parts may be added or eliminated, without departing from the scope of the invention. Some of these variations are described further below, but no specific embodiment(s) should be construed to limit the scope of the invention as defined by the appended claims.

Housing 206 may be flexible or rigid in various embodiments. In some embodiments, for example, flexible housing 206 may be comprised of multiple segments configured such that housing 206 is deformable by tensioning a tensioning cord coupled to the segments. In some embodiments, housing 206 is formed from an elastic material having a geometry selected to engage and optionally shape or constrict the valve annulus. For example, the rings may be formed from super-elastic material, shape memory alloy such as Nitinol, spring stainless steel, or the like. In other instances, housing 206 could be formed from an inflatable or other structure can be selectively rigidified in situ, such as a gooseneck or lockable element shaft, any of the rigidifying structures described above, or any other rigidifying structure.

"Anchors," for the purposes of this application, is defined to mean any fasteners. Thus, anchors 210 may comprise C-shaped or semicircular hooks, curved hooks of other shapes, straight hooks, barbed hooks, clips of any kind, T-tags, or any other suitable fastener(s). In one embodiment, as described above, anchors may comprise two tips that curve in opposite directions upon deployment, forming two intersecting semi-circles, circles, ovals, helices or the like. In some embodiments, anchors 210 are self-deforming. By "self-deforming" it is meant that anchors 210 change from a first undeployed shape to a second deployed shape upon release of anchors 210 from restraint in housing 206. Such self-deforming anchors 210 may change shape as they are released from housing 206 and enter valve annulus tissue, to secure themselves to the tissue. Thus, a crimping device or other similar mechanism is not required on distal end 202 to apply force to anchors 210 to attach them to annular tissue. Self-deforming anchors 210 may be made of any suitable material, such as a super-elastic or shape-memory material like Nitinol or spring stainless steel. In other embodiments, anchors 210 may be made of a non-shape-memory material and made be loaded into housing 206 in such a way that they change shape upon release. Alternatively, anchors 210 that are not self-deforming may be used, and such anchors may be secured to tissue via crimping, firing or the like. Even self-securing anchors may be crimped in some embodiments, to provide enhanced attachment to tissue. Delivery of anchors may be accomplished by any suitable device and technique, such as by simply releasing the anchors by hydraulic balloon delivery as discussed further below. Any number, size and shape of anchors 210 may be included in housing 206.

In one embodiment, anchors 210 are generally C-shaped or semicircular in their undeployed form, with the ends of the C being sharpened to penetrate tissue. Midway along the C-shaped anchor 210, an eyelet may be formed for allowing slidable passage of tether 212. To maintain anchors 210 in their C-shaped, undeployed state, anchors 210 may be retained within housing 206 by two mandrels 214, one mandrel 214 retaining each of the two arms of the C-shape of each anchor 210. Mandrels 214 may be retractable within elongate catheter body 204 to release anchors 210 and allow them to change from their undeployed C-shape to a deployed shape. The deployed shape, for example, may approximate a complete circle or a circle with overlapping ends, the latter appearing similar to a key ring. Such anchors are described further below, but generally may be advantageous in their ability to secure themselves to annular tissue by changing from their undeployed to their deployed shape. In some embodiments, anchors 210 are also configured to lie flush with a tissue surface after being deployed. By "flush" it is meant that no significant amount of an anchor protrudes from the surface, although some small portion may protrude.

Tether 212 may be one long piece of material or two or more pieces and may comprise any suitable material, such as suture, suture-like material, a Dacron strip or the like. Retaining mandrels 214 may also have any suitable configuration and be made of any suitable material, such as stainless steel, titanium, Nitinol, or the like. Various embodiments may have one mandrel, two mandrels, or more than two mandrels.

In some embodiments, anchors 210 may be released from mandrels 214 to contact and secure themselves to annular tissue without any further force applied by delivery device 200. Some embodiments, however, may also include one or more expandable members 208, which may be expanded to help drive anchors 210 into tissue. Expandable member(s) 208 may have any suitable size and configuration and may be made of any suitable material(s). Hydraulic systems such as expandable members are known in the art, and any known or as yet undiscovered expandable member may be included in housing 206 as part of the present invention.

Figure 4:
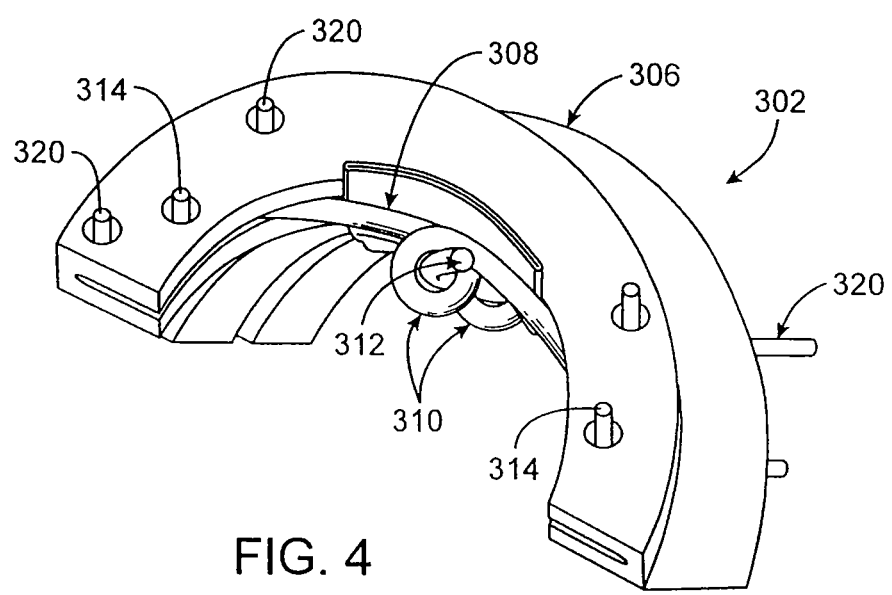
FIG. 4. is a perspective view of a segment of a distal portion of an anchor delivery device, with anchors in an undeployed shape and position.
Figure 5:
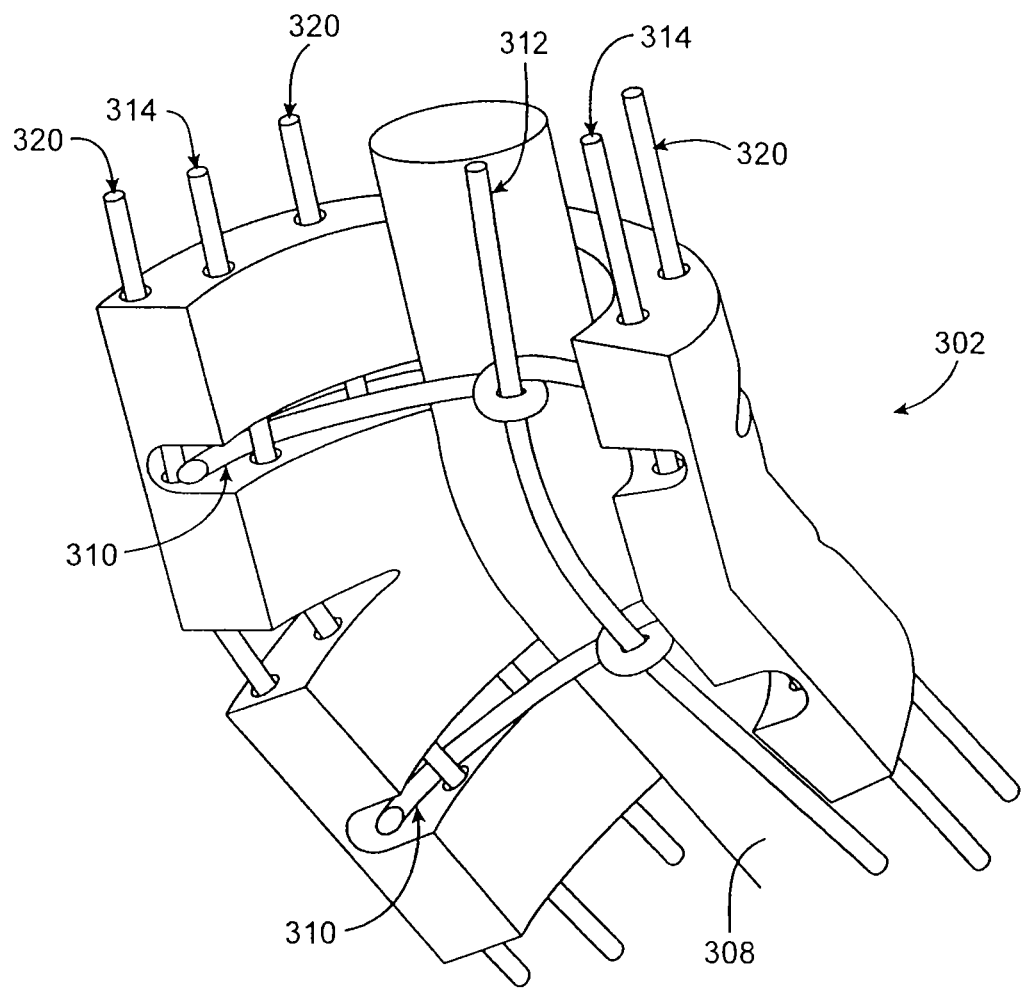
FIG. 5 is a different perspective view of the segment of the device shown in FIG. 4.

Referring now to FIGS. 4 and 5, a segment of a distal portion 302 of an anchor delivery device suitably includes a housing. 306, multiple tensioning cords 320 for applying tension to housing 306 to change its shape, two anchor retaining mandrels 314 slidably disposed in housing 306, multiple anchors 310 slidably coupled with a tether 312, and an expandable member 308 disposed between anchors 310 and housing 306. As can be seen in FIGS. 4 and 5, housing 306 may include multiple segments to allow the overall shape of housing 306 to be changed by applying tension to tensioning cords 320. As also is evident from the drawings, "C-shaped" anchors 310 may actually have an almost straight configuration when retained by mandrels 314 in housing 306. Thus, for the purposes of this application, "C-shaped" or "semicircular" refers to a very broad range of shapes including a portion of a circle, a slightly curved line, a slightly curved line with an eyelet at one point along the line, and the like.

Figure 6:
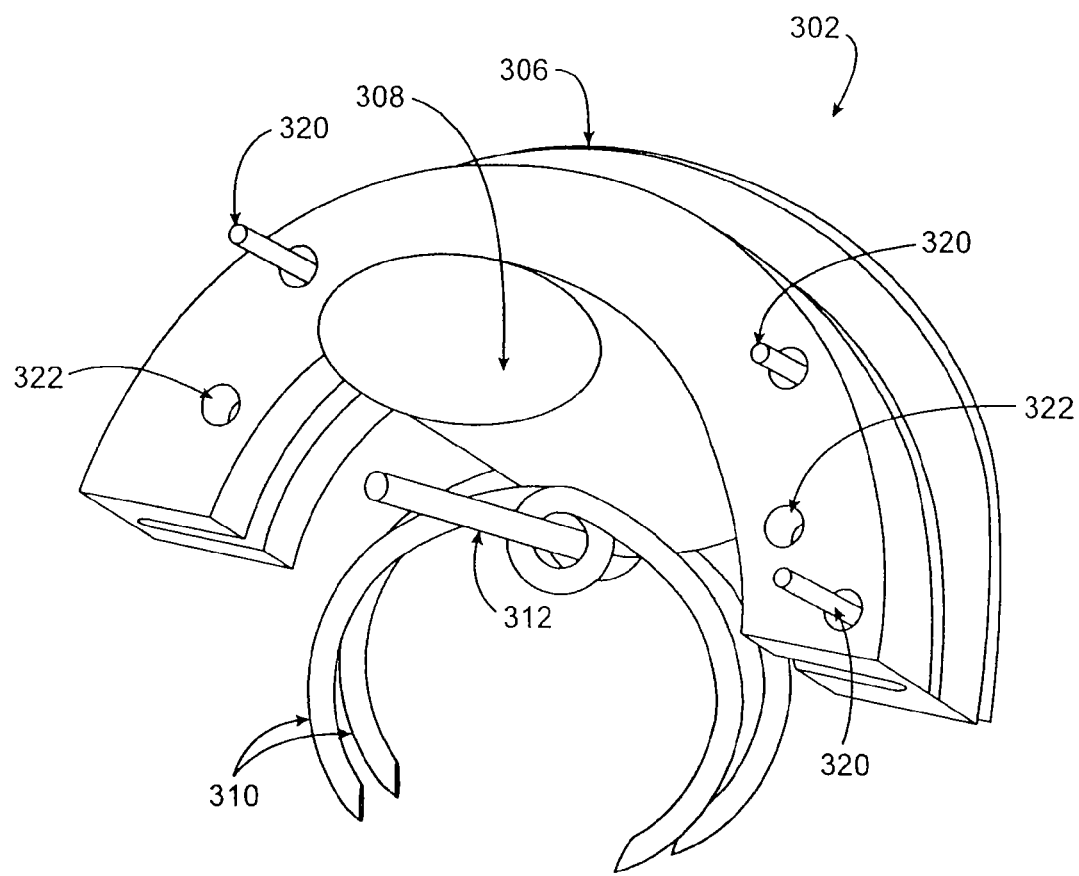
FIG. 6. is a perspective view of a segment of a distal portion of an anchor delivery device, with anchors in a deployed shape and position.

With reference now to FIG. 6, the same segment of distal portion 302 is shown, but mandrels 314 have been withdrawn from two mandrel apertures 322, to release anchors 310 from housing 306. Additionally, expandable member 308 has been expanded to drive anchors out of housing 306. Anchors 310, having been released from mandrels 314, have begun to change from their undeployed, retained shape to their deployed, released shape.

Figure 7A:
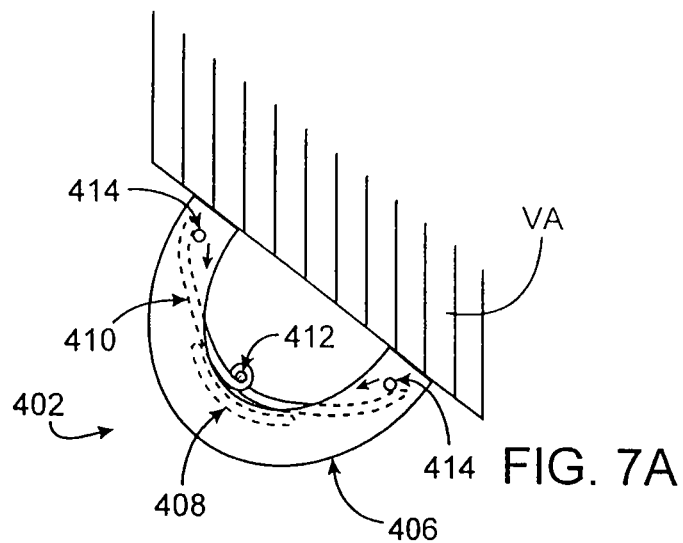
FIGS. 7A-7E are cross-sectional views of an anchor delivery device, illustrating a method for delivering anchors to valve annulus tissue, according to one embodiment of the invention.

Referring now to FIGS. 7A-7E, a cross-section of a distal portion 402 of an anchor delivery device is shown in various stages of delivering an anchor to tissue of a valve annulus VA. In FIG. 7A, distal portion 402 is positioned against the valve annulus, an anchor 410 is retained by two mandrels 414, a tether 412 is slidably disposed through an eyelet on anchor 410, and an expandable member 408 is coupled with housing 406 in a position to drive anchor 410 out of housing 406. When retained by mandrels 414, anchor 410 is in its undeployed shape. As discussed above, mandrels 414 may be slidably retracted, as designated by the solid-tipped arrows in FIG. 7A, to release anchor 410. In various embodiments, anchors 410 may be released one at a time, such as by retracting mandrels 414 slowly, may be released in groups, or may all be released simultaneously, such as by rapid retraction of mandrels 414.

Figure 7B:
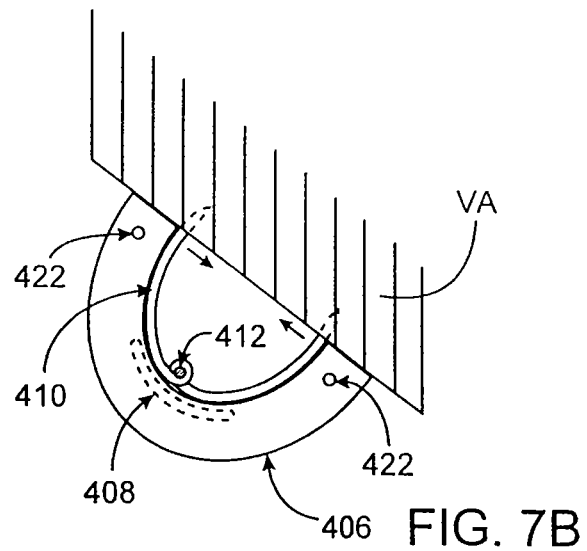
Figure 7C:
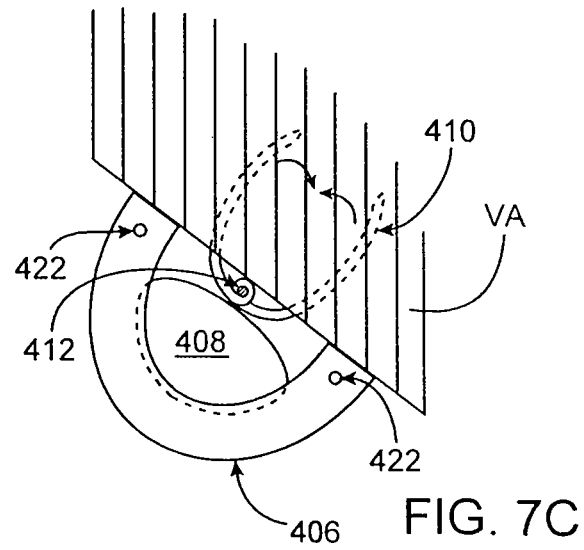
Figure 7D:
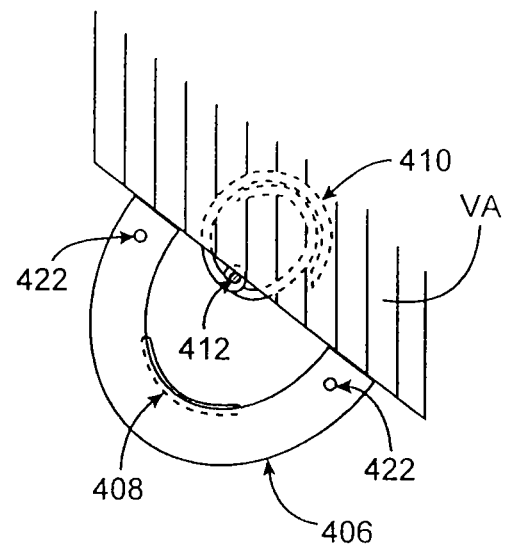
Figure 7E:
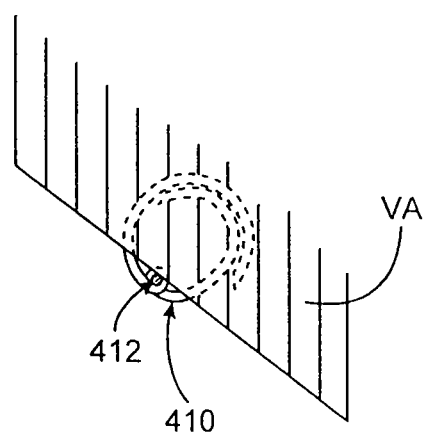

In FIG. 7B, anchor 410 has begun to change from its undeployed shape to its deployed shape (as demonstrated by the hollow-tipped arrows) and has also begun to penetrate the annular tissue VA. Empty mandrel apertures 422 demonstrate that mandrels 414 have been retracted at least far enough to release anchor 410. In FIG. 7B, expandable member 408 has been expanded to drive anchor 410 partially out of housing 406 and further into the valve annulus VA. Anchor 410 also continues to move from its undeployed towards its deployed shape, as shown by the hollow-tipped arrows. In FIG. 7D, anchor 410 has reached its deployed shape, which is roughly a completed circle with overlapping ends or a "key ring" shape. In FIG. 7E, delivery device 402 has been removed, leaving a tethered anchor in place in the valve annulus. Of course, there will typically be a plurality of tethered anchors secured to the annular tissue. Tether 412 may then be cinched to apply force to anchors 410 and cinch and tighten the valve annulus.

Figure 8A:
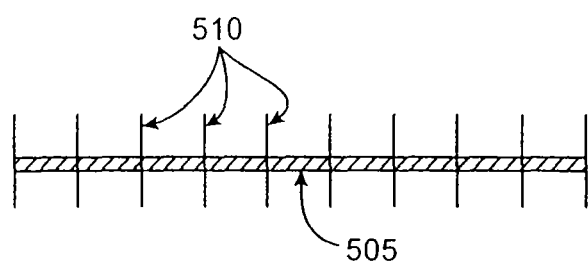
FIGS. 8A and 8B are top-views of a plurality of anchors coupled to a self-deforming coupling member or "backbone," with the backbone shown in an undeployed shape and a deployed shape.
Figure 8B:
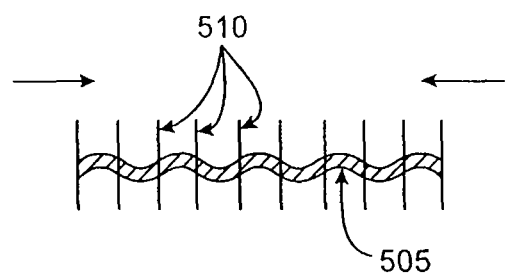

With reference now to FIGS. 8A and 8B, a diagrammatic representation of another embodiment of coupled anchors is shown. Here, anchors 510 are coupled to a self-deforming or deformable coupling member or backbone 505. Backbone 505 may be fabricated, for example, from Nitinol, spring stainless steel, or the like, and may have any suitable size or configuration. In one embodiment, as in FIG. 8A, backbone 505 is shaped as a generally straight line when held in an undeployed state, such as when restrained within a housing of an anchor deliver device. When released from the delivery device, backbone 505 may change to a deployed shape having multiple bends, as shown in FIG. 8B. By bending, backbone 505 shortens the longitudinal distance between anchors, as demonstrated by the solid-tipped arrows in FIG. 8B. This shortening process may act to cinch a valve annulus into which anchors 510 have be secured. Thus, anchors 510 coupled to backbone 505 may be used to cinch a valve annulus without using a tether or applying tethering force. Alternatively, a tether may also be coupled with anchors 510 to further cinch the annulus. In such an embodiment, backbone 505 will be at least partially conformable or cinchable, such that when force is applied to anchors 510 and backbone 505 via a tether, backbone 505 bends further to allow further cinching of the annulus.

Figure 9A:
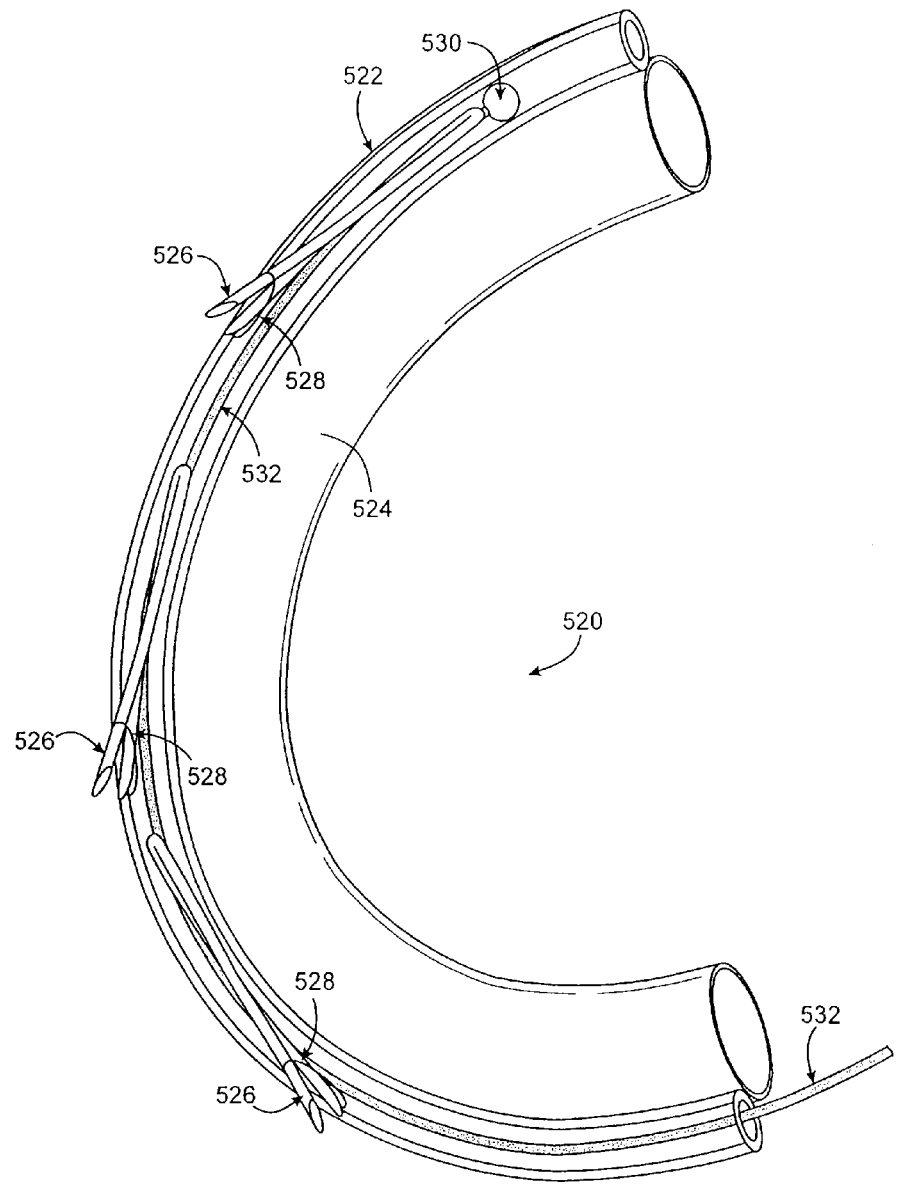
FIGS. 9A-9C are various perspective views of a distal portion of a flexible anchor delivery device according to one embodiment of the present invention.
Figure 9B:
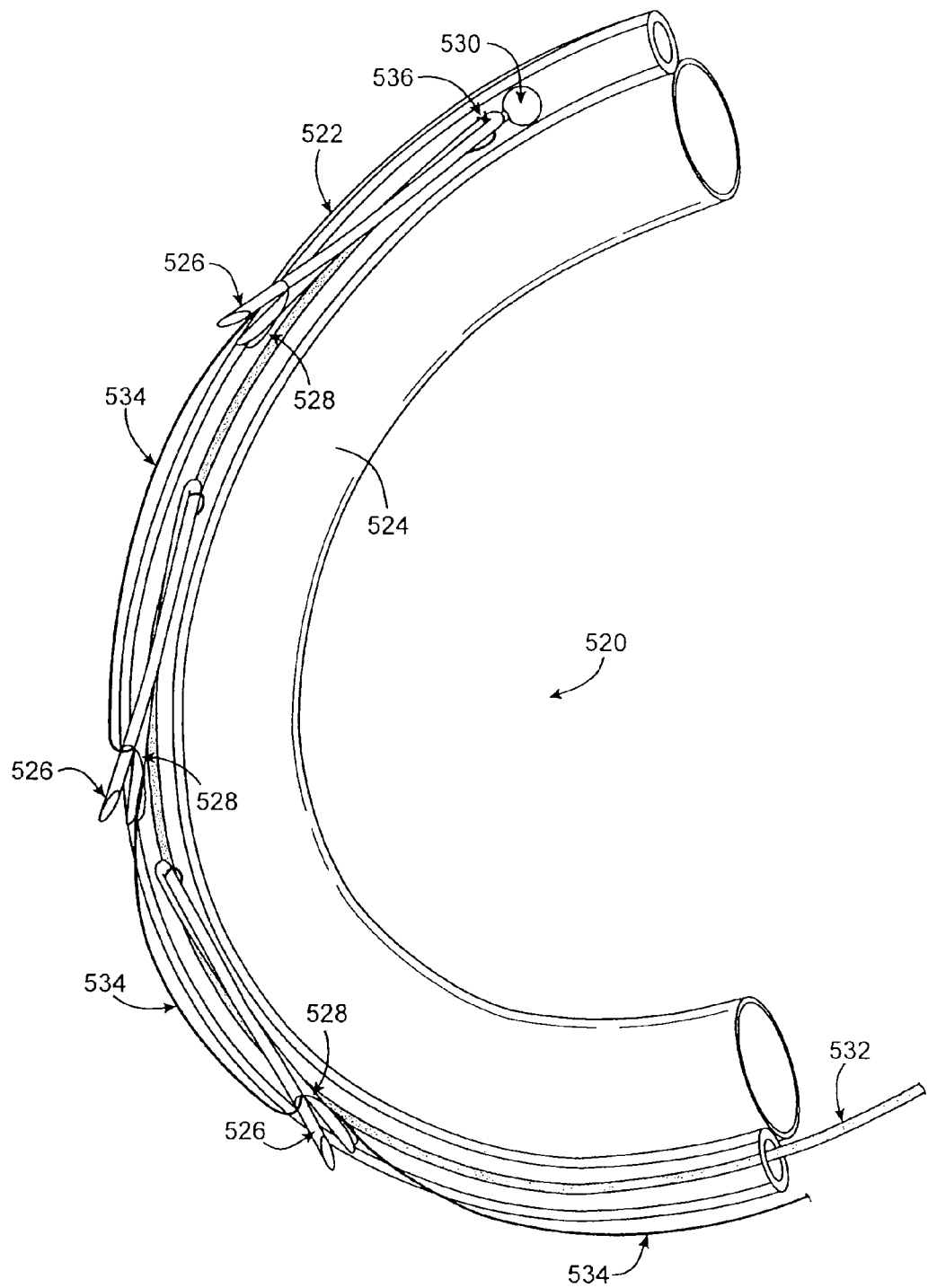
Figure 9C:
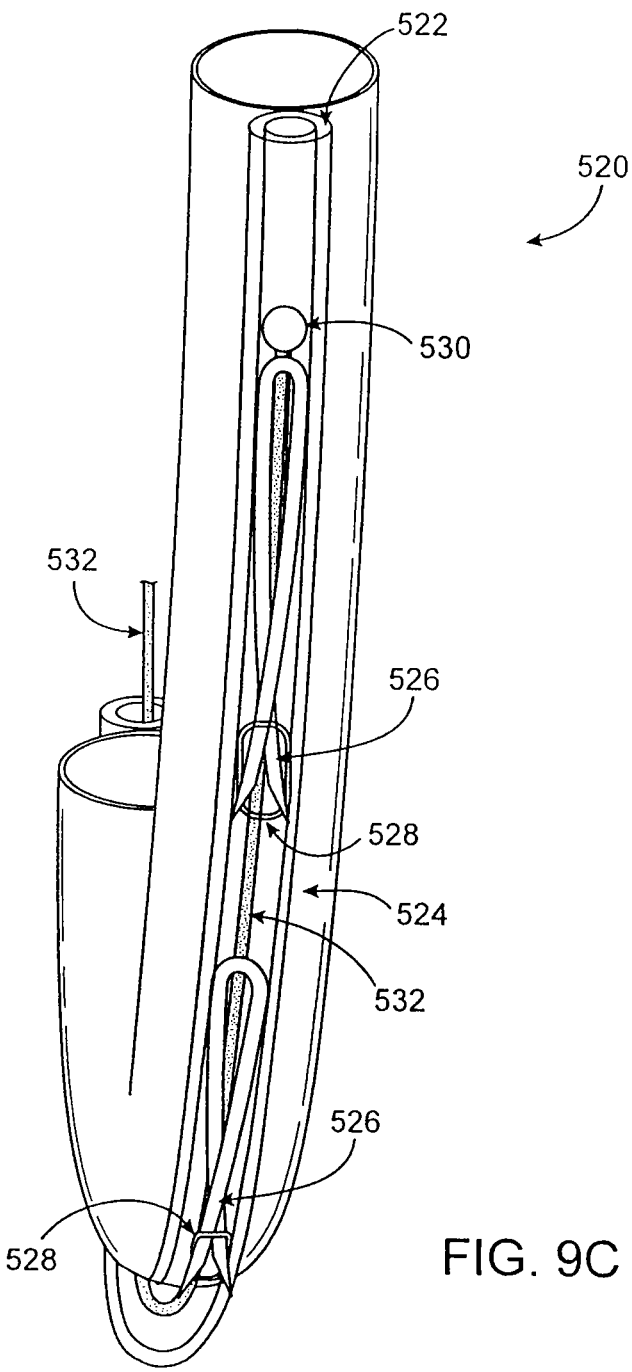

Referring now to FIGS. 9A-9C, in one embodiment a flexible distal portion of an anchor delivery device 520 suitably includes a housing 522 coupled with an expandable member 524. Housing 522 may be configured to house multiple coupled anchors 526 and an anchor contacting member 530 coupled with a pull cord 532. Housing 522 may also include multiple apertures 528 for allowing egress of anchors 526. For clarity, delivery device 520 is shown without a tether in FIGS. 9A and 9C, but FIG. 9B shows that a tether 534 may extend through an eyelet, loop or other portion of each anchor 526, and may exit each aperture 528 to allow for release of the plurality of anchors 526. The various features of this embodiment are described further below.

In the embodiment shown in FIGS. 9A-9C, anchors 526 are relatively straight and lie relatively in parallel with the long axis of delivery device 522. Anchor contacting member 530, which may comprise any suitable device, such as a ball, plate, hook, knot, plunger, piston, or the like, generally has an outer diameter that is nearly equal to or slightly less than the inner diameter of housing 522. Contacting member 530 is disposed within the housing, distal to a distal-most anchor 526, and is retracted relative to housing 522 by pulling pull cord 532. When retracted, anchor contacting member 530 contacts and applies force to a distal-most anchor 526 to release cause that anchor 526 to exit housing 522 via one of the apertures 528. Contacting member 530 is then pulled farther proximally to contact and apply force to the next anchor 526 to deploy that anchor 526, and so on.

Retracting contacting member 530 to push anchors 526 out of apertures 528 may help cause anchors 526 to avidly secure themselves to adjacent tissue. Using anchors 526 that are relatively straight/flat when undeployed allows anchors 526 with relatively large deployed sizes to be disposed in (and delivered from) a relatively small housing 522. In one embodiment, for example, anchors 526 that deploy into a shape approximating two intersecting semi-circles, circles, ovals, helices, or the like, and that have a radius of one of the semi-circles of about 3 mm may be-disposed within a housing 522 having a diameter of about 5 French (1.67 mm) and more preferably 4 French (1.35 mm) or even smaller. Such anchors 526 may measure about 6 mm or more in their widest dimension. These are only examples, however, and other larger or smaller anchors 526 may be disposed within a larger or smaller housing 522. Furthermore, any convenient number of anchors 526 may be disposed within housing 522. In one embodiment, for example, housing 522 may hold about 1-20 anchors 526, and more preferably about 3-10 anchors 526. Other embodiments may hold more anchors 526.

Anchor contacting member 530 and pull cord 532 may have any suitable configuration and may be manufactured from any material or combination of materials. In alternative embodiments, contacting member 530 may be pushed by a pusher member to contact and deploy anchors 526. Alternatively, any of the anchor deployment devices and methods previously described may be used.

Tether 534, as shown in FIG. 9B, may comprise any of the tethers 534 or tether-like devices already described above, or any other suitable device. Tether 534 is generally attached to a distal-most anchor 526 at an attachment point 536. The attachment itself may be achieved via a knot, weld, adhesive, or by any other suitable attachment means. Tether 234 then extends through an eyelet, loop or other similar configuration on each on each of the anchors 526 so as to be slidably coupled with the anchors 526. In the embodiment shown, tether 534 exits each aperture 528, then enters the next-most-proximal aperture, passes slidably through a loop on an anchor 526, and exits the same aperture 528. By entering and exiting each aperture 528, tether 534 allows the plurality of anchors 526 to be deployed into tissue and cinched. Other configurations of housing 522, anchors 526 and tether 534 may alternatively be used. For example, housing 522 may include a longitudinal slit through which tether 534 may pass, thus allowing tether 534 to reside wholly within housing before deployment.

Expandable member 524 is an optional feature of anchor delivery device 520, and thus may be included in some embodiments and not in others. In other words, a distal portion of anchor delivery device 520 may include housing, contents of housing, and other features either with or without an attached expandable member. Expandable member 524 may comprise any suitable expandable member currently known or discovered in the future, and any method and substance(s) may be used to expand expandable member 524. Typically, expandable member 524 will be coupled with a surface of housing 522, will have a larger radius than housing 522, and will be configured such that when it is expanded as housing 522 nears or contacts the valve annulus, expandable member 524 will push or press housing 522 into enhanced contact with the annulus. For example, expandable member 524 may be configured to expand within a space near the corner formed by a left ventricular wall and a mitral valve leaflet.

Figure 10B:
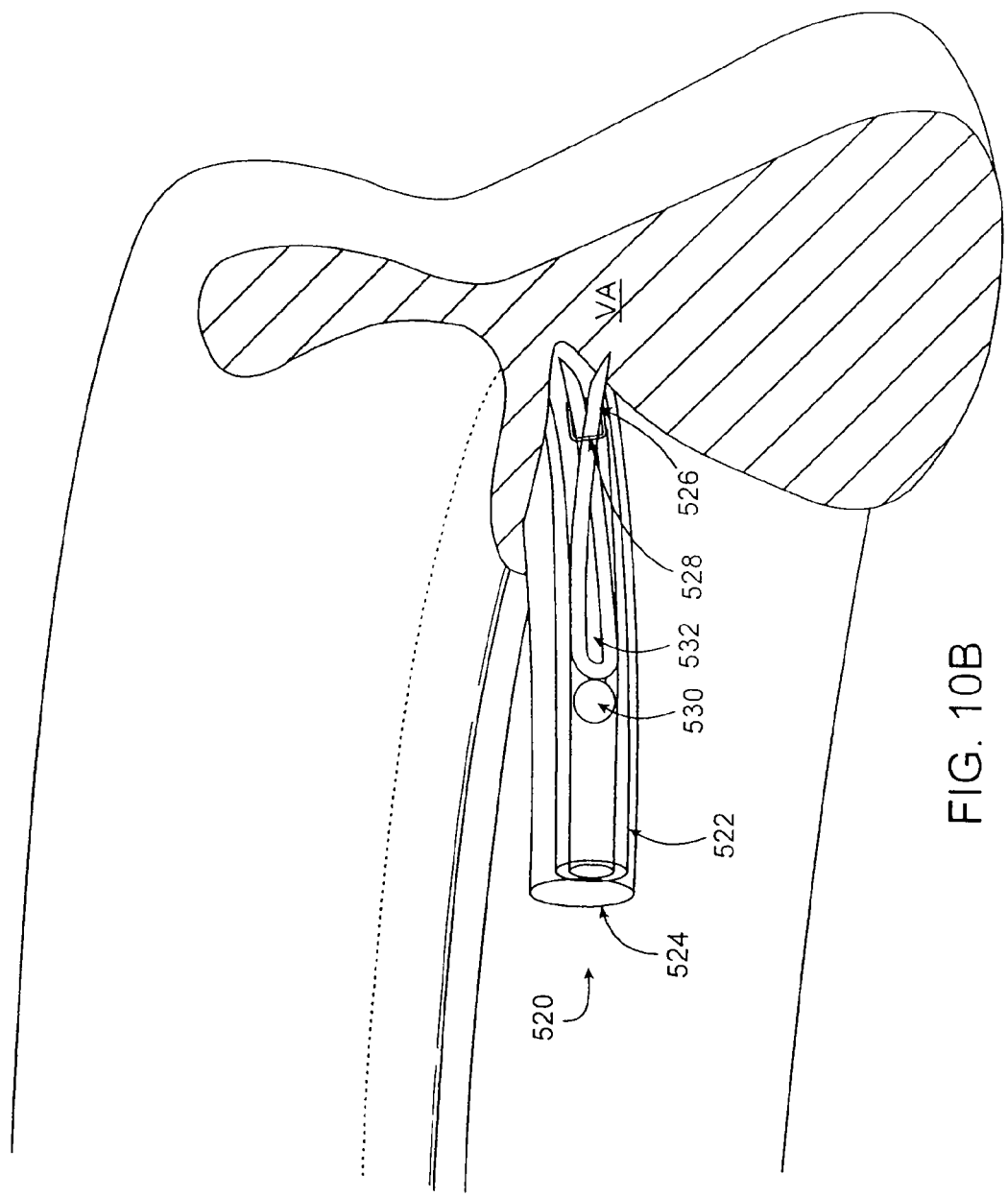

With reference now to FIGS. 10A-10F, a method is shown for applying a plurality of tethered anchors 526 to a valve annulus VA in a heart. As shown in FIG. 10A, an anchor delivery device 520 is first contacted with the valve annulus VA such that openings 528 are oriented to deploy anchors 526 into the annulus. Such orientation may be achieved by any suitable technique. In one embodiment, for example, a housing 522 having an elliptical cross-sectional shape may be used to orient openings 528. As just described, contact between housing 522 and the valve annulus VA may be enhanced by expanding expandable member 524 to wedge housing within a corner adjacent the annulus.

Generally, delivery device 520 may be advanced into any suitable location for treating any valve by any suitable advancing or device placement method. Many catheter-based, minimally invasive devices and methods for performing intravascular procedures, for example, are well known, and any such devices and methods, as well as any other devices or method later developed, may be used to advance or position delivery device 520 in a desired location. For example, in one embodiment a steerable guide catheter is first advanced in retrograde fashion through an aorta, typically via access from a femoral artery. The steerable catheter is passed into the left ventricle of the heart and thus into the space formed by the mitral valve leaflets, the left ventricular wall and cordae tendineae of the left ventricle. Once in this space, the steerable catheter is easily advanced along a portion (or all) of the circumference of the mitral valve. A sheath is advanced over the steerable catheter within the space below the valve leaflets, and the steerable catheter is removed through the sheath. Anchor delivery device 520 may then be advanced through the sheath to a desired position within the space, and the sheath may be removed. In some cases, an expandable member coupled to delivery device 520 may be expanded to wedge or otherwise move delivery device 520 into the corner formed by the left ventricular wall and the valve leaflets to enhance its contact with the valve annulus. Of course, this is but one exemplary method for advancing delivery device 520 to a position for treating a valve, and any other suitable method, combination of devices, etc. may be used.

As shown in FIG. 10B, when delivery device 520 is positioned in a desired location for deploying anchors 526, anchor contacting member 530 is retracted to contact and apply force to a most-distal anchor 526 to begin deploying anchor 526 through aperture 528 and into tissue of the valve annulus VA. FIG. 10C show anchor 526 further deployed out of aperture 528 and into valve annulus VA. FIG. 10D shows the valve annulus VA transparently so that further deployment of anchors 526 can be seen. As shown, in one embodiment of the invention, anchors 526 include two sharpened tips that move in opposite directions upon release from housing 522 and upon contacting the valve annulus VA. Between the two sharpened tips, an anchor 526 may be looped or have any other suitable eyelet or other device for allowing slidable coupling with a tether 534.

Figure 10E:
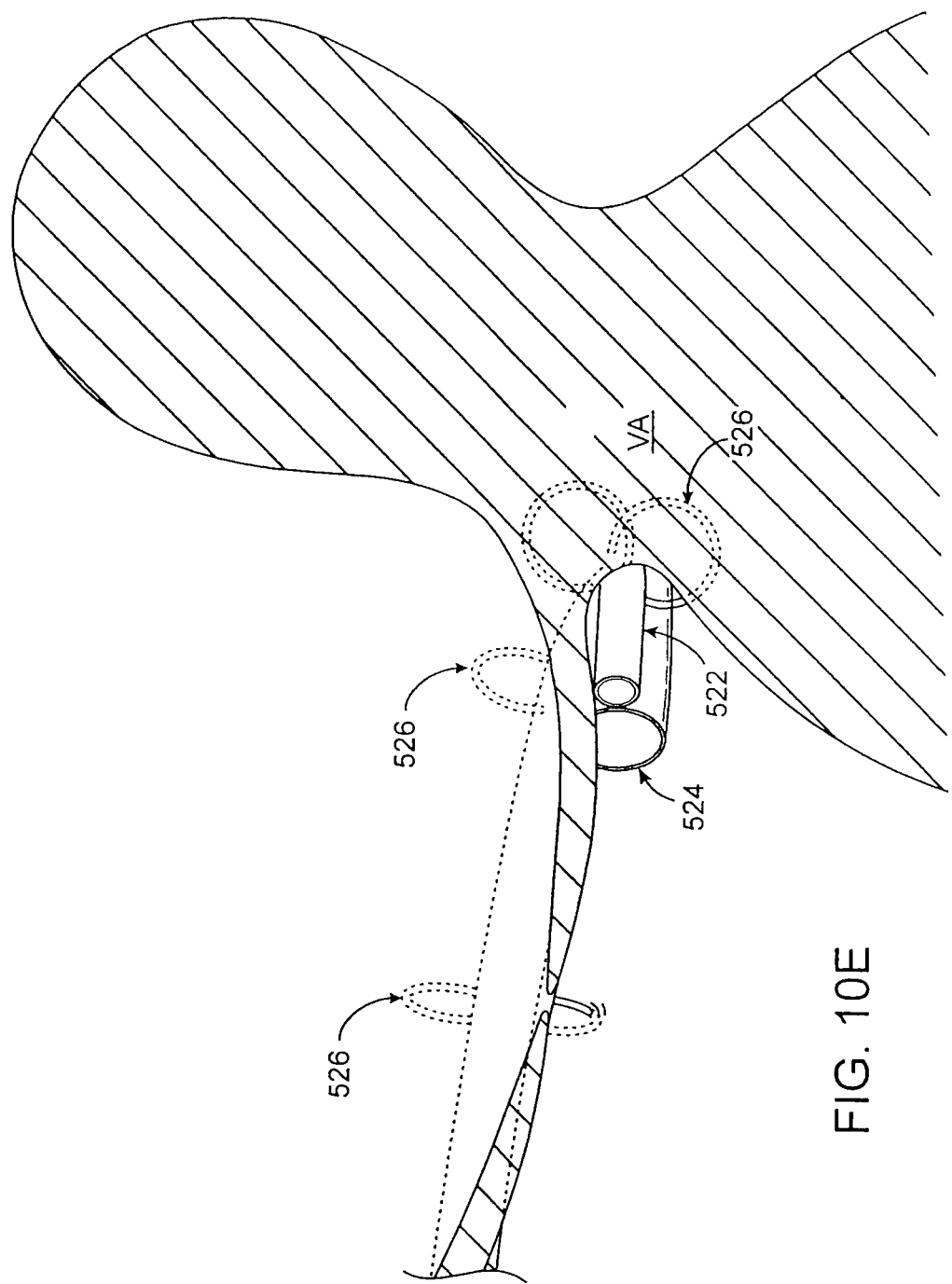

Referring now to FIG. 10E, anchors 526 are seen in their fully deployed or nearly fully deployed shape, with each pointed tip (or "arm") of each anchor 526 having curved to form a circle or semi-circle. Of course, in various embodiments anchors 526 may have any other suitable deployed and undeployed shapes, as described more fully above. FIG. 1 OF shows anchors 526 deployed into the valve annulus VA and coupled with tether 534, with the distal-most anchor 526 coupled attached fixedly to tether 524 at attachment point 536. At this stage, tether 534 may be cinched to tighten the annulus, thus reducing valve regurgitation. In some embodiments, valve function may be monitored by means such as echocardiogram and/or fluoroscopy, and tether 534 may be cinched, loosened, and adjusted to achieve a desired amount of tightening as evident via the employed visualization technique(s). When a desired amount of tightening is achieved, tether 534 is then attached to a most-proximal anchor 526 (or two or more most-proximal anchors 526), using any suitable technique, and tether 534 is then cut proximal to the most-proximal anchor 526, thus leaving the cinched, tethered anchors 526 in place along the valve annulus VA. Attachment of tether 534 to the most-proximal anchor(s) 526 may be achieved via adhesive, knotting, crimping, tying or any other technique, and cutting tether 534 may also be performed via any technique, such as with a cutting member coupled with housing 522.

In one embodiment, cinching tether 534, attaching tether 534 to most-proximal anchor 526, and cutting tether 534 are achieved using a termination device (not shown). The termination device may comprise, for example, a catheter advancable over tether 534 that includes a cutting member and a nitinol knot or other attachment member for attaching tether 534 to most-proximal anchor. The termination catheter may be advanced over tether 534 to a location at or near the proximal end of the tethered anchors 526. It may then be used to apply opposing force to the most-proximal anchor 526 while tether 534 is cinched. Attachment and cutting members may then be used to attach tether 534 to most-proximal anchor 526 and cut tether 534 just proximal to most-proximal anchor 526. Such a termination device is only one possible way of accomplishing the cinching, attachment and cutting steps, and any other suitable device(s) or technique(s) may be used.

In some embodiments, it may be advantageous to deploy a first number of anchors 526 along a first portion of a valve annulus VA, cinch the first anchors to tighten that portion of the annulus, move the delivery device 520 to another portion of the annulus, and deploy and cinch a second number of anchors 526 along a second portion of the annulus. Such a method may be more convenient, in some cases, than extending delivery device 520 around all or most of the circumference of the annulus, and may allow a shorter, more maneuverable housing 522 to be used. In some embodiments, for example, an anterior portion of a valve annulus may first be tightened, and then a posterior portion may be tightened.

Although the foregoing is a complete and accurate description of the present invention, the description provided above is for exemplary purposes only, and variations may be made to the embodiments described without departing from the scope of the invention. Thus, the above description should not be construed to limit the scope of the invention as described in the appended claims.

What is claimed is:

1. A device for applying coupled anchors to an annulus of a heart valve, the device comprising:
 a flexible elongate shaft having a proximal end and a distal end; a housing adjacent the distal end, the housing comprising a lumen;
 a coupled anchor assembly comprising a plurality of coupled anchors disposed within the lumen of the housing at respective deployment positions along the housing; and
 at least one anchor contacting member for causing the anchors to be delivered from their deployment positions along the housing and to tissue at or adjacent to an annulus of a heart valve at locations along the tissue corresponding to the deployment positions along the housing
 wherein the housing comprises a plurality of openings at or near the deployment positions and in communication with the lumen, and wherein the at least one anchor contacting member is configured to deliver the plurality of coupled anchors through the plurality of openings to release the plurality of coupled anchors from the housing.

2. A device as in claim 1, wherein the elongate shaft comprises a flexible catheter which may be advanced intravascularly to the heart to contact the annulus.

3. A device as in claim 2, wherein the flexible catheter may be advanced through an aorta and into a left ventricle of the heart to contact the tissue at or adjacent to the valve annulus.

4. A device as in claim 2, wherein the housing has a cross-sectional diameter of about 1.67 mm or less and a radius of each anchor, when deployed from the housing, is at least about 3 mm.

5. A device as in claim 2, wherein the housing holds at least 10 anchors.

6. A device as in claim 1, wherein the housing is sufficiently flexible to be conformable to the tissue at or adjacent to the annulus.

7. A device as in claim 6, wherein the housing conforms to the tissue at or adjacent to the annulus at an intersection of a left ventricular wall and one or more mitral valve leaflets of the heart.

8. A device as in claim 7, further comprising at least one expandable member coupled with the housing for expanding to urge the housing toward the intersection to enhance contact of the housing with the tissue at or adjacent to the valve annulus.

9. A device as in claim 7, wherein the housing has an oval or elliptical shape for helping to orient an anchor delivery surface of the housing to contact the tissue at or adjacent to the valve annulus.

10. A device as in claim 6, wherein the housing is coupled with an actuator for deforming the housing to conform it to the tissue at or adjacent to the annulus.

11. A device as in claim 6, wherein the housing is coupled with a shaped expandable member which expands to deform the housing to conform it to the tissue at or adjacent to the annulus.

12. A device as in claim 11, wherein the housing has a cross-sectional shape selected from the group consisting of a semicircle, a circle, an oval and a partial oval.

13. A device as in claim 12, wherein each opening is sized to allow one of the plurality of anchors to pass therethrough.

14. A device as in claim 13, wherein the coupled anchor assembly comprises a tether, the anchors being slidably coupled with the tether.

15. A device as in claim 14, wherein each of the plurality of anchors includes at least one eyelet, and the tether passes through the at least one eyelet of each anchor.

16. A device as in claim 15, wherein the coupled anchor assembly comprises a longitudinally shortenable coupling member to which the anchors are mounted, the coupling member changeable from a longer, undeployed state to a shorter, deployed state to constrict the tissue at or adjacent to the annulus.

17. A device as in claim 16, wherein the coupling member comprises a self-deforming coupling member fixedly coupled with each anchor, the coupling member movable from the longer, undeployed state to the shorter, deployed state.

18. A device as in claim 17, wherein the coupling member moves from the longer, undeployed state to the shorter, deployed state after release from the housing.

19. A device as in claim 15, further comprising at least one crimping member for crimping the coupled anchors to secure them to the tissue at or adjacent to the annulus.

20. A device as in claim 15, wherein the anchors are coupled with a self-deforming coupling member fixedly coupled with each anchor, the self-deforming member changing from an undeployed shape to a deployed shape upon release from the housing to constrict the tissue at or adjacent to the annulus.

21. A device as in claim 20, wherein the coupling member comprises a super-elastic or shape-memory member having an undeployed shape approximating a straight line and a deployed shape of a line having multiple bends.

22. A device as in claim 15, wherein the at least one anchor contacting member comprises at least one retractable force applying device which, when retracted proximally relative to the housing, sequentially contacts the anchors to apply force to the anchors such that they exit the housing via the plurality of openings in the housing.

23. A device as in claim 22, wherein the retractable force applying device comprises at least one circular member having a diameter approximating or slightly less than an inner diameter of the housing, and further comprising an actuator at or near the proximal end of the shaft for affecting the anchor contacting member, and wherein the actuator comprises a tether, cord or wire coupled at its distal end with the circular member.

24. A device as in claim 23, wherein the at least one circular member has a shape selected from the group consisting of a sphere, an oblong or ovoid ball, a plate, a plunger, an anchor, a hook, and a knot.

25. A device as in claim 23, wherein the at least one anchor contacting member comprises at least one retaining member for retaining the anchors within the housing, wherein the at least one actuator moves the retaining member to release the anchors from the housing.

26. A device as in claim 25, wherein the at least one retaining member comprises at least one anchor retaining mandrel, slidably disposed in the housing so that retracting the mandrel releases one or more of the anchors.

27. A device as in claim 26, wherein the at least one mandrel comprises two mandrels, each mandrel positioned to retain an arm of each anchor.

28. A device as in claim 23, wherein the at least one actuator includes means for cinching the coupled anchors to reduce the circumference of the valve annulus.

29. A device as in claim 23, wherein the at least one actuator is selected from the group consisting of a trigger, a handle, a plunger, a squeeze-activated device, a syringe-grip device and a foot-operated device.

30. A device as in claim 14, wherein the tether is disposed along the anchors so as to be positioned between the anchors and the tissue at or adjacent to the annulus when the anchors are deployed.

31. A device as in claim 14, further comprising a termination device slidably advanced over the tether, the termination device comprising:
at least one attachment member for attaching the tether to at least a terminal anchor of the plurality of anchors; and
at least one cutting member for cutting the tether to leave the tethered anchors secured to the tissue at or adjacent to the annulus.

32. A device as in claim 31, wherein the termination device comprises at least one relatively stiff portion near its distal end for applying opposing force against the terminal anchor while tether is cinched.

33. A device as in claim 14, wherein the tether is cinchable, and further comprising at least one fastener coupled with the tether for securing the tether to at least one of the anchors after cinching the tether.

34. A device as in claim 33, wherein the at least one fastener comprises a knot made of super-elastic or shape-memory material.

35. A device as in claim 11, wherein each anchor has an undeployed shape when constrained in the housing by the at least one retaining member and elastically expands to a deployed shape when released from the housing.

36. A device as in claim 35, wherein the undeployed shape of each anchor is relatively straight, with each anchor having two sharpened tips, and wherein each anchor curves upon deployment, with the two tips curving in opposite directions.

37. A device as in claim 36, wherein the deployed shape of each anchor comprises first and second intersecting shapes, with an eyelet for passage of a slidable tether disposed at the intersection of the intersecting shapes.

38. A device as in claim 37, wherein the intersecting shapes are selected from the group consisting of one or more of circles, semicircles, helices, overlapping helices and ovals.

39. A device as in claim 35, wherein each anchor has an opened arcuate undeployed shape and assumes a closed shape with overlapping ends after release from constraint.

40. A device as in claim 39, wherein the undeployed shape is approximately a C-shape or semicircle having two sharpened ends, and the deployed shape is a closed circle in which the two ends overlap, wherein upon release from the delivery device the anchors secure to the tissue at or adjacent to the annulus by penetrating the tissue with the ends and subsequently assuming the closed circle shape.

41. A device as in claim 39, wherein the anchors lie flush with the tissue at or adjacent to the annulus of the valve when secured to the tissue.

42. A device as in claim 39, wherein the anchors comprise at least one super-elastic or shape-memory material.

43. A device as in claim 6, wherein the housing comprises a shape-changing portion.

44. A device as in claim 43, further comprising at least a first tensioning cord coupled with the shape-changing portion for applying tension to the shape-changing portion to cause it to bend in at least a first direction.

45. A device as in claim 44, further comprising at least a second tensioning cord coupled with the shape-changing portion for applying tension to the shape-changing portion to cause it to bend in at least a second direction.

46. A device as in claim 45, wherein the first direction comprises approximately a C-shape for conforming to the tissue at or adjacent to the annulus and the second direction comprises an upward or proximal direction for applying force to the tissue at or adjacent to the annulus.

47. A device as in claim 44, wherein the shape-changing portion includes multiple notches along at least one side to control bending into a curve which conforms to the shape of the tissue at or adjacent to the annulus.

48. A device as in claim 44, wherein the shape-changing portion comprises multiple stacked segments coupled with at least the first tensioning member to control bending into the shape of the tissue at or adjacent to the annulus.

49. A device as in claim 44, wherein the shape-changing portion comprises a shape-memory material configured to conform to the shape of the tissue at or adjacent to the annulus.

50. A device as in claim 49, wherein the shape-changing portion further comprises at least one lumen for introducing a fluid to cause the shape-memory material to conform to the shape of the tissue at or adjacent to the annulus.

51. A device as in claim 1, further comprising at least one expandable member disposed within the housing for pushing the anchors out of the housing.

52. A device as in claim 1 further comprising at least one actuator at or near the proximal end of the shaft for affecting the anchor contacting member to cause delivery of the anchors to the tissue at or adjacent to the annulus at locations along the valve tissue corresponding to the deployment positions along the housing.

53. A device as in claim 1 further comprising a fluid powered member disposed within the housing for selectively driving the anchors out of the housing.

54. A device for applying multiple tethered anchors to tissue at or adjacent to an annulus of a heart valve, the device comprising:
  a flexible elongate catheter having a distal portion for delivering the tethered anchors, the distal portion having a lumen and a cross-sectional diameter of about 1.67 mm or less;
  a plurality of tethered anchors disposed within the lumen of the distal portion, each anchor having a radius of at least about 3 mm when deployed from the catheter; and
  at least one anchor delivery member coupled with the catheter for causing the anchors to be delivered from the catheter,
  wherein the distal portion comprises a plurality of openings in communication with the lumen, and wherein the at least one anchor delivery member is configured to contact the plurality of tethered anchors to deliver them through the plurality of openings and release the plurality of tethered anchors from the distal portion.

* * * * *